United States Patent [19]

Bandman et al.

[11] Patent Number: 5,858,708
[45] Date of Patent: Jan. 12, 1999

[54] POLYNUCLEOTIDES ENCODING TWO NOVEL HUMAN NEUROENDOCRINE-SPECIFIC PROTEINS

[76] Inventors: Olga Bandman, 2309 Rock St. No. 27, Mountain View, Calif. 94043; Janice Au-Young, 1419 Kains Ave., Berkeley, Calif. 94702; Surya K. Goli, 620 Iris Ave. No. 338, Sunnyvale, Calif. 94086; Jennifer L. Hillman, 467 N. 3rd St. Apt. #3, San Jose, Calif. 95112

[21] Appl. No.: 700,607

[22] Filed: Aug. 12, 1996

[51] Int. Cl.$^6$ ............................. C12N 15/12; C12N 15/85
[52] U.S. Cl. ...................... 435/69.1; 536/23.1; 536/23.5; 435/325; 435/320.1
[58] Field of Search ................................ 536/23.5, 24.31, 536/23.1; 435/69.1, 240.1, 320.1, 252.3, 325; 935/11

[56] References Cited

PUBLICATIONS van de Velde, H.J., et al., "NSP-encoded reticulons, neuroendocrine proteins of a novel gene family associated with membranes of the endoplasmic reticulum" *J Cell Sci* 107:2403–2416 (1994).

van de Velde, H.J., et al., "Molecular analysis of expression in rat brain of NSP–A, a novel neuroendocrine–specific protein of the endoplasmic reticulum" *Brain Res. Mol. Brain Res.* 23:81–92 (1994).

Roebroek, A.J., et al., "Cloning and expression of alternative transcripts of a novel neuroendocrine–specific gene and identification of its 135–kDa translational product" *J Biol Chem* 268:13429–47 (1993).

Wieczorek, D.F., et al., "Developmentally regulated cDNA expressed exclusively in neural tissue" *Brain Res. Mol. Brain Res.* 10:33–41 (1991).

Takeda, J., et al., "A molecular inventory of human pancreatic islets: sequence analysis of 1000 cDNA clones" *Hum Mol Genet* 2:1793–8 (1993).

Martin–Gallardo, A., et al., "Automated DNA sequencing and analysis of 106 kilobases from human chromosome 19q13.3" *Nat Genet* 1:34–9 (1992).

Senden, N.H., et al., "Subcellular localization and supramolecular organization of neuroendocrine–specific protein B (NSP–B) in small cell lung cancer" *Eur. J. Cell Biol.* 65:341–53 (1994).

Jackson, M.R., et al., "Retrieval of transmembrane proteins to the endoplasmic reticulum" *J Cell Biol* 121:317–33 (1993).

Collard, J.F., et al. "Defective axonal transport in a transgenic mouse model of amyotrophic lateral sclerosis" *Nature* 375:61–4 (1995).

Mourelatos, Z., et al., "The Golgi apparatus of spinal cord motor neurons in transgenic mice expressing mutant Cu, Zn superoxide dismutase becomes fragmented in early, preclinical stages of the disease" *Proc. Natl. Acad. Sci, U.S.A.* 93:5472–5477 (1996).

van de Velde, H.J., et al., "NSP–encoded reticulons are neuroendocrine markers of a novel category in human lung cancer diagnosis" *Cancer Res.* 54:4769–76 (1994).

Senden, N.H., et al., "Cluster–10 lung–cancer antibodies recognize NSPs, novel neuro–endocrine proteins associated with membranes of the endoplasmic reticulum" *Int J Cancer Suppl* 8:84–8 (1994).

Roebroek et al. (GI 307307, GenBank Sequence Database (Accession 307307), National Center for Biotechnology Information, National Library of Medicine, Bethesda, Maryland 2084 (1993).

Robroek et al. (GI 307309), GenBank Sequence Database (Accession 307309), National Center for Biotechnology Information, National Library of Medicine, Bethesda, Maryland 2084 (1993).

Roebroek et al. (GI 307311), GenBank Sequence Database (Accession 307311), National Center for Biotechnology Information, National Library of Medicine, Bethesda, Maryland 2084 (1993).

Wieczorek et al. (GI 281046), GenBank Sequence Database (Accession 281046), National Center for Biotechnology Information, National Library of Medicine, Bethesda, Maryland 2084 (1991).

Rudinger In "Peptide Hormones" (Jun. 1976) ed. J.A. Parsons, University Park Press Baltimore, pp. 1–7.

Hillier et al. GenBank/EST–STS Sequence database, Accession No. R62718, human clone 138831 (Submitted May 26, 1995).

Hillier et al. GenBank/EST–STS Sequence database, Accession No. R22276, human clone 130873 (Submitted Apr. 18, 1995).

Bell et al GenBank/EST.STS Sequence database, Accession No. T10889, human clone hbc043 (Submitted Nov. 29, 1993).

*Primary Examiner*—Paula K. Hutzell
*Assistant Examiner*—Robert C. Hayes
*Attorney, Agent, or Firm*—Lucy J. Billings

[57] ABSTRACT

The present invention provides polynucleotides which identify and encode two novel human NSP-like proteins (NSPLP). The invention provides for genetically engineered expression vectors and host cells comprising the nucleic acid sequences encoding NSPLP. The invention also provides for the use of substantially purified NSPLP, antagonists, and in pharmaceutical compositions for the treatment of diseases associated with the expression of NSPLP. Additionally, the invention provides for the use of antisense molecules to NSPLP in pharmaceutical compositions for treatment of diseases associated with the expression of NSPLP. The invention also describes diagnostic assays which utilize diagnostic compositions comprising the polynucleotide, fragments or the complement thereof, which hybridize with the genomic sequence or the transcript of polynucleotides encoding NSPLP or anti-NSPLP antibodies which specifically bind to NSPLP.

12 Claims, 24 Drawing Sheets

```
     11              20              29         38              47         56
5' TTT GTG CAG TTA CAG CTT TTC TNT TGG TAT GCA TAA TTA ATA NTT GGA GCT GCA 65              74              83         92             101        110
AAG AGA TCG TGA CAA GAG ATG GAC GGT CAG AAG AAA AAT TGG AAG GAC AAG GTT
                         M   D   G   Q   K   K   N   W   K   D   K   V 119             128             137        146             155        164
GTT GAC CTC CTG TAC TGG AGA GAC ATT AAG AAG ACT GGA GTG TTT GGT GCC
 V   D   L   L   Y   W   R   D   I   K   K   T   G   V   F   G   A 173             182             191        200             209        218
AGC CTA TTC CTG CTG CTT TCA TTG ACA GTA TTC AGC ATT GTG AGC GTA ACA GCC
 S   L   F   L   L   L   S   L   T   V   F   S   I   V   S   V   T   A 227             236             245        254             263        272
TAC ATT GCC TTG GCC CTG CTC TCT GTG ACC ATC AGC TTT AGG ATA TAC AAG GGT
 Y   I   A   L   A   L   L   S   V   T   I   S   F   R   I   Y   K   G 281             290             299        308             317        326
GTG ATC CAA GCT ATC CAG AAA TCA GAT GAA GGC CAC CCA TTC AGG GCA TAT CTG
 V   I   Q   A   I   Q   K   S   D   E   G   H   P   F   R   A   Y   L 335             344             353        362             371        380
GAA TCT GAA GTT GCT ATA TCT GAG GAG TTG GTT CAG AAG TAC AGT AAT TCT GCT
 E   S   E   V   A   I   S   E   E   L   V   Q   K   Y   S   N   S   A

Fig. 1A
```

```
    389            398            407            416            425            432
CTT GGT CAT    GTG AAC TGC    ACG ATA AAG    GAA CTC AGG    CGC CTC TTC    TTA GTT GAT
 L   G   H      V   N   C      T   I   K      E   L   R      R   L   F      L   V   D 443            452            461            470            479            488
GAT TTA GTT    GAT TCT CTG    AAG TTT GCA    GTG TTG ATG    TGG GTA TTT    ACC TAT GTT
 D   L   V      D   S   L      K   F   A      V   L   M      W   V   F      T   Y   V 497            506            515            524            533            542
GGT GCC TTG    TTT AAT GGT    CTG ACA CTA    CTG ATT TTG    GCT CTC ATT    TCA CTC TTC
 G   A   L      F   N   G      L   T   L      L   I   L      A   L   I      S   L   F 551            560            569            578            587            596
AGT GTT CCT    GTT ATT TAT    GAA CGG CAG    GCA CAT CAG    ATA GAT CAT    TAT CTA GGA
 S   V   P      V   I   Y      E   R   Q      A   H   Q      I   D   H      Y   L   G 605            614            623            632            641            650
CTT GCA AAT    AAG AAT GTT    AAA GAT GCT    ATG GCT AAA    ATC CAA GCA    AAA ATC CCT
 L   A   N      K   N   V      K   D   A      M   A   K      I   Q   A      K   I   P 659            668            677            686            695            704
GGA TTG AAG    CGC AAA GCT    GAA TGA CGC    AAA CGC CCA    AAA TAA TTA    GTA GGA GTT CAT
 G   L   K      R   K   A      E
```

Fig. 1B

```
      713         722         731         740         749         758
CTT TAA AGG GGA TAT TCA TTT GAT TAT ACG GGG GAG GGT CAG GGA GAG ACG ACC 767         776         785         794
TTG ACG TTG CAG TGC AGT TTC ACA GAT CGT TGT TAG ATC TT 3
```

Fig. 1C

```
                                            9              18             27             36             45         54
5' CAC NAG CGN NTC GNG CTC CCG AAC CTC TAG CTG CGA CTC GGA NTG AGT CAG TCA 63             72             81             90             99            108
GTC TGT CGG AGT CTG TCC TCG GAG CAG GCG GAG AGG GAC TTG AGC GAG CCA 117            126            135            144            153            162
GTT GCC GGA TTA TTC TAT TTC CCC TCC CTC TCT CCC GCC CCG TAT CTC TTT TCA 171            180            189            198            207            216
TTT TNN CAC CCT TGC TCG CGT ANC ATG GCG GAG CGT NCG GCG GCC ACT CAG
                                          M   A   E   R   X   A   A   T   Q 225            234            243            252            261            270
TCC CAT TCC ATC TCC TCG TCG TTC GGA GCC GAG CCG TCC GCG CCC GGC GGC
 S   H   S   I   S   S   S   F   G   A   E   P   S   A   P   G   G 279            288            297            306            315            324
GGC GGG AGC CCA GGA GCC TGC CCC GCC CTG GGG ACG AAG AGC TGC AGC TCC
 G   G   S   P   G   A   C   P   A   L   G   T   K   S   C   S   S 333            342            351            360            369            378
TGT GCG GTG CAC GAT CTG ATT TTM TGG AGA GAT GTG AAG AAG ACT GGG TTT GTC
 C   A   V   H   D   L   I   X   W   R   D   V   K   K   T   G   F   V
```

Fig. 2A

```
      387         396         405         414         423         432
TTT GGC ACC ACG CTG ATC ATG CTG CTT TCC CTG GCA GCT TTC AGT GTC ATC AGT
 F   G   T   T   L   I   M   L   L   S   L   A   A   F   S   V   I   S 441         450         459         468         477         486
GTG GTT TCT TAC CTC ATC CTG GCT CTT CTC TCT GTC ACC ATC AGC TTC AGG ATC
 V   V   S   Y   L   I   L   A   L   L   S   V   T   I   S   F   R   I 495         504         513         522         531         540
TAC AAG TCC GTC ATC CAA GCT GTA CAG AAG TCA GAA GAA GGC CAT CCA TTC AAA
 Y   K   S   V   I   Q   A   V   Q   K   S   E   E   G   H   P   F   K 549         558         567         576         585         594
GCC TAC CTG GAC GTA GAC ATT ACT CTG TCC TCA GAA GCT TTC CAT AAT TAC ATG
 A   Y   L   D   V   D   I   T   L   S   S   E   A   F   H   N   Y   M 603         612         621         630         639         648
AAT GCT GCC ATG GTG CAC ATC AAC AGG GCC CTG AAA CTC ATT CGT CTC TTT
 N   A   A   M   V   H   I   N   R   A   L   K   L   I   R   L   F 657         666         675         684         693         702
CTG GTA GAA GAT CTG GTT GAC TCC TTG AAG CTG GCT GTC TTC ATG TGG CTG ATG
 L   V   E   D   L   V   D   S   L   K   L   A   V   F   M   W   L   M 711         720         729         738         747         756
ACC TAT GTT GGT GCT GTT TTT AAC GGA ATC ACC CTT CTA ATT CTT GCT GAA CTG
 T   Y   V   G   A   V   F   N   G   I   T   L   L   I   L   A   E   L
```

Fig. 2B

```
       765               774               783               792               801              810
CTC ATT TTN AGT GTC CCG ATT GTN TAT NAG AAG TAC AAG GTT CCA AGC AAA ACT
 L   I   X   S   V   P   I   V   Y   X   K   Y   K   V   P   S   K   T 819               828               837               846               855              864
CCC TGG AAT CGC CAA AAA AAA GGC AGA ATA AGT ACA TGG AAA CCA GAA ATG CAA
 P   W   N   R   Q   K   K   G   R   I   S   T   W   K   P   E   M   Q 873               882               891               900               909              918
CAG TTA CTA AAA CAC CAT TTA ATA GTT ATA ACG TCG TTA CTT GTA CTA TGA AGG
 Q   L   L   K   H   H   L   I   V   I   T   S   L   L   V   L 927               936               945               954               963              972
AAA ATA CTC AGT GTC AGC TTG AGC CTG CAT TCC AAG CTT TTT TAA TTT GGT 981               990               999              1008              1017             1026
GGT TTT CTC CCA TCC TTT CCC TTT AAC CCT CAG TNT CAA GCA CAA ANT TTN ATG 1035              1044              1053              1062              1071             1080
GAC TGA TAA NNG ATC TAT NTT AGA NCT CAG AAG ANG ANA GNT TCA NNT GCA TAG

1089
GNT AAG GNA NTA CC 3'
```

Fig. 2C

| | | | |
|---|---|---|---|
| CORNNOT01 | corneal fibroblasts, 76y | 4 | 0.3996 |
| FIBRAGT02 | ATGD60 fibroblasts, ataxia telan, radiation 30 min | 2 | 0.3968 |
| BLADNOT01 | bladder, 78 F | 10 | 0.3494 |
| OVARNON01 | ovary, 59 F, NORM | 2 | 0.3185 |
| U937NOT01 | U937 monocyte cell line, 37 M | 6 | 0.2973 |
| FIBRNOT01 | WI38 lung fibroblast cell line, fetal F | 6 | 0.2812 |
| SCORNON02 | spinal cord, 71 M, NORM | 7 | 0.2415 |
| COCHFEM01 | ear, cochlea, fetal, WM | 2 | 0.2315 |
| KIDNNOT01 | kidney, 64 F | 1 | 0.1562 |
| BRSTTUT02 | breast tumor, 54 F, match to BRSTNOT03 | 5 | 0.1489 |
| PANCTUT02 | pancreatic tumor, carcinoma, 45 F | 5 | 0.1402 |
| SCORNON01 | spinal cord, 71 M, NORM | 1 | 0.1379 |
| BRSTNOT01 | breast, 56 F | 7 | 0.1345 |
| BRAINOT03 | brain, 26 M | 7 | 0.1297 |
| BLADTUT02 | bladder tumor, carcinoma, 80 F | 4 | 0.1220 |
| PROSTUT05 | prostate tumor, 69 M, match to PROSNOT07 | 4 | 0.1212 |
| BSTMNOT01 | brain stem, 72 M | 1 | 0.1203 |
| PROSTUT04 | prostate tumor, 57 M, match to PROSNOT06 | 7 | 0.1140 |
| MPHGNOT03 | macrophages (adher PBMNC), M/F | 8 | 0.1032 |
| HMC1NOT01 | HMC-1 mast cell line, 52 F | 3 | 0.0999 |
| SPLNFEM01 | spleen, fetal, WM | 3 | 0.0995 |
| MMLR3DT01 | macrophages (adher PBMNC), M/F, 72-hr MLR | 3 | 0.0993 |
| BRAINOT11 | brain, right temporal, epilepsy, 5 M | 3 | 0.0966 |
| MMLR1DT01 | macrophages (adher PBMNC), M/F, 24-hr MLR | 4 | 0.0944 |
| NEUTGMT01 | granulocytes, periph blood, M/F, treated GM-CSF | 6 | 0.0938 |
| RETNNOM02 | retina, 55 M, NORM, WM | 1 | 0.0899 |
| MUSCNOT01 | muscle, skeletal | 2 | 0.0888 |
| RATRNOT01 | heart, right atrium, 51 F | 1 | 0.0861 |

Fig. 3A

| | | | |
|---|---|---|---|
| LUNGNOM01 | lung, 72 M, WM | 3 | 0.0802 |
| BRAINOT09 | brain, fetal M | 3 | 0.0783 |
| MUSCNOT02 | muscle, psoas, 12 M | 2 | 0.0763 |
| TLYMNOT02 | lymphocytes (non-adher PBMNC), M/F | 3 | 0.0761 |
| PROSNOT01 | prostate, 78 M | 2 | 0.0696 |
| NEUTLPT01 | granulocytes, periph blood, M/F, treated LPS | 4 | 0.0671 |
| UTRSNOT02 | uterus, 34 F | 4 | 0.0666 |
| BSTMNON02 | brain stem, 72 M, NORM | 2 | 0.0637 |
| STOMNOT02 | stomach, 52 M, match to STOMTUT01 | 2 | 0.0615 |
| SCORNOT01 | spinal cord, 71 M | 3 | 0.0603 |
| TONGTUT01 | tongue tumor, carcinoma, 36 M | 2 | 0.0590 |
| BRAITUT08 | brain tumor, astrocytoma, 47 M | 4 | 0.0582 |
| PROSNOT05 | prostate, 67 M, match to PROSTUT03 | 1 | 0.0575 |
| LATRTUT02 | heart tumor, myoma, 43 M | 4 | 0.0548 |
| SYNOOAT01 | synovium, knee, osteoarthritis, 82 F | 3 | 0.0538 |
| HIPONOT01 | brain, hippocampus, 72 F | 1 | 0.0535 |
| PENITUT01 | penis tumor, carcinoma, 64 M | 2 | 0.0532 |
| KIDNNOT09 | kidney, fetal M | 2 | 0.0531 |
| SYNORAT04 | synovium, wrist, rheumatoid, 62 F | 3 | 0.0521 |
| BRAITUT02 | brain tumor, metastasis, 58 M | 3 | 0.0507 |
| MENITUT03 | brain tumor, benign meningioma, 35 F | 2 | 0.0499 |
| PLACNOT02 | placenta, fetal F | 3 | 0.0495 |
| THP1PEB01 | THP-1 promonocyte cell line, treated PMA | 1 | 0.0487 |
| MPHGNOT02 | macrophages (adher PBMNC), 24 M | 1 | 0.0478 |
| BRSTNOT02 | breast, 55 F, match to BRSTTUT01 | 3 | 0.0475 |
| RATRNOT02 | heart, right atrium, 39 M | 2 | 0.0472 |
| COLNCRT01 | colon, Crohn's, 40 M, match to COLNNOT05 | 1 | 0.0468 |

Fig. 3B

| | | | |
|---|---|---|---|
| LVENNOT01 | heart, left ventricle, 51 F | 1 | 0.0450 |
| PLACNOB01 | placenta, neonatal F | 2 | 0.0450 |
| BRSTTUT03 | breast tumor, 58 F, match to BRSTNOT05 | 3 | 0.0444 |
| PLACNOM02 | placenta, neonatal F, NORM, WM | 8 | 0.0444 |
| COLNNOT01 | colon, 75 M, match to COLNTUT02 | 2 | 0.0426 |
| BRSTNOM02 | breast, F, NORM, WM | 2 | 0.0413 |
| THP1PLB02 | THP-1 promonocyte cell line, treated PMA, LPS | 1 | 0.0407 |
| BRAITUT01 | brain tumor, oligoastrocytoma, 50 F | 3 | 0.0403 |
| KERANOT02 | keratinocytes, primary cell line, 30 F | 1 | 0.0396 |
| THYMNOT02 | thymus, 3 M | 2 | 0.0386 |
| HNT2AGT01 | hNT-2 cell line, post-mitotic neurons | 2 | 0.0380 |
| STOMTUT01 | stomach tumor, 52 M, match to STOMNOT02 | 1 | 0.0367 |
| MMLR2DT01 | macrophages (adher PBMNC), M/F, 48-hr MLR | 2 | 0.0354 |
| SPLNFET01 | spleen, fetal | 1 | 0.0352 |
| PROSNOT07 | prostate, 69 M, match to PROSTUT05 | 1 | 0.0347 |
| TONSNOT01 | tonsil, hyperplasia, 6 M | 1 | 0.0339 |
| LUNGNOT01 | lung, 72 M | 1 | 0.0338 |
| PROSNOT06 | prostate, 57 M, match to PROSTUT04 | 1 | 0.0332 |
| PGANNOT03 | paraganglia, 46 M | 2 | 0.0309 |
| PROSTUT01 | prostate tumor, 50 M, match to PROSNOT02 | 1 | 0.0309 |
| BRAITUT03 | brain tumor, astrocytoma, 17 F | 1 | 0.0307 |
| BEPINOT01 | bronchial epithelium, primary cell line, 54 M | 1 | 0.0304 |
| BRSTTUT01 | breast tumor, 55 F, match to BRSTNOT02 | 2 | 0.0302 |
| STOMNOT01 | stomach, 55 M | 1 | 0.0300 |
| BRAINOT12 | brain, right frontal, epilepsy, 5 M | 1 | 0.0299 |
| BRSTNOT03 | breast, 54 F, match to BRSTTUT02 | 2 | 0.0293 |
| SYNORAT05 | synovium, knee, rheumatoid, 62 F | 1 | 0.0286 |

Fig. 3C

| | | |
|---|---|---|
| LUNGNOT09 | lung, fetal M | 1 0.0285 |
| TESTTUT02 | testicular tumor, 31 M | 1 0.0278 |
| THYRNOT03 | thyroid tumor, adenoma, 28 F | 2 0.0276 |
| COLNTUT03 | colon tumor, 62 M, match to COLNNOT16 | 1 0.0272 |
| HYPONOB01 | hypothalamus, 16-75 M/F | 1 0.0270 |
| BRSTNOM01 | breast, F, NORM, WM | 1 0.0264 |
| LATRNOT01 | heart, left atrium, 51 F | 1 0.0263 |
| LIVRNOM01 | liver, 49 M, WM | 1 0.0254 |
| PANCNOT08 | pancreas, 65 F, match to PANCTUT01 | 1 0.0254 |
| TMLR3DT01 | lymphocytes (non-adher PBMNC), M, 96-hr MLR | 1 0.0229 |
| SPLNNOT02 | spleen, 29 M | 1 0.0220 |
| MELANOM01 | melanocytes, M, NORM, WM | 2 0.0216 |
| TMLR2DT01 | lymphocytes (non-adher PBMNC), M/F, 24-hr MLR | 1 0.0211 |
| EOSIHET02 | eosinophils, hypereosinophilia, 48 M | 2 0.0209 |
| LUNGNOT03 | lung, 79 M, match to LUNGTUT02 | 1 0.0200 |
| SYNORAB01 | synovium, hip, rheumatoid, 68 F | 1 0.0195 |
| CERVNOT01 | cervix, 35 F | 1 0.0193 |
| LUNGTUT02 | lung tumor, metastasis, 79 M, match to LUNGNOT03 | 1 0.0189 |
| LUNGNOT04 | lung, 2 M | 1 0.0183 |
| NEUTFMT01 | granulocytes, periph blood, M/F, treated fMLP | 1 0.0174 |
| KIDNNOT05 | kidney, neonatal F | 1 0.0161 |
| PGANNOT01 | paraganglia, 46 M | 1 0.0160 |
| NGANNOT01 | ganglioneuroma, 9 M | 1 0.0155 |
| BRSTNOT05 | breast, 58 F, match to BRSTTUT03 | 1 0.0154 |
| CORPNOT02 | brain, corpus callosum, Alzheimer's, 74 M | 1 0.0151 |
| COLNFET02 | colon, fetal F | 1 0.0142 |
| LUNGFET03 | lung, fetal F | 1 0.0137 |

Fig. 3D

| | | |
|---|---|---|
| UCMCL5T01 | lymphocytes (umbilical cord), treated IL-5 | 1 0.0125 |
| LIVSFEM02 | liver/spleen, fetal M, NORM, WM | 3 0.0087 |
| BRAINOM01 | brain, infant F, NORM, WM | 1 0.0045 |

Fig. 3E

| | | | |
|---|---|---|---|
| ADRENOT01 | adrenal gland, 10-46 M/F | 2 | 0.2081 |
| BRAINOT03 | brain, 26 M | 11 | 0.2039 |
| NEUTLPT01 | granulocytes, periph blood, M/F, treated LPS | 10 | 0.1678 |
| SCORNON01 | spinal cord, 71 M, NORM | 1 | 0.1379 |
| OLFENOM01 | epithelium, olfactory, 35 F, WM | 1 | 0.1330 |
| THP1NOB01 | THP-1 promonocyte cell line, control | 4 | 0.1309 |
| BMARNOR02 | bone marrow, 16-70 M/F, RP | 3 | 0.1294 |
| BRAINOT11 | brain, right temporal, epilepsy, 5 M | 4 | 0.1288 |
| BRSTNOM02 | breast, F, NORM, WM | 6 | 0.1239 |
| HIPONOT01 | brain, hippocampus, 72 F | 2 | 0.1070 |
| BRAINOT04 | brain, choroid plexus, hemorrhage, 44 M | 3 | 0.1067 |
| SCORNON02 | spinal cord, 71 M, NORM | 3 | 0.1035 |
| LUNGNOT01 | lung, 72 M | 3 | 0.1014 |
| THP1PEB01 | THP-1 promonocyte cell line, treated PMA | 2 | 0.0975 |
| KIDNNOT02 | kidney, 64 F | 2 | 0.0964 |
| BRSTNOT01 | breast, 56 F | 5 | 0.0960 |
| PITUNOT02 | pituitary, 7-65 M/F | 2 | 0.0905 |
| RETNNOM02 | retina, 55 M, NORM, WM | 1 | 0.0899 |
| BRAINOT12 | brain, right frontal, epilepsy, 5 M | 3 | 0.0898 |
| MUSCNOT02 | muscle, psoas, 12 M | 2 | 0.0763 |
| OVARNOM01 | ovary, 49 F, WM | 1 | 0.0752 |
| EOSIHET02 | eosinophils, hypereosinophilia, 48 M | 7 | 0.0731 |
| HEARNOT01 | heart, 56 M | 1 | 0.0707 |
| KIDNNOT05 | kidney, neonatal F | 4 | 0.0645 |
| NEUTGMT01 | granulocytes, periph blood, M/F, treated GM-CSF | 4 | 0.0625 |
| BRSTNOT07 | breast, 43 F | 2 | 0.0614 |

Fig. 4A

| | | | |
|---|---|---|---|
| SCORNOT01 | spinal cord, 71 M | 3 | 0.0603 |
| HNT2RAT01 | hNT-2 cell line, teratocarcinoma, treated RA | 3 | 0.0556 |
| LATRTUT02 | heart tumor, myoma, 43 M | 4 | 0.0548 |
| HUVELPB01 | HUVEC endothelial cell line, treated cytokine, LPS | 1 | 0.0546 |
| BRAITUT01 | brain tumor, oligoastrocytoma, 50 F | 4 | 0.0537 |
| PANCNOT04 | pancreas, 5 M | 1 | 0.0504 |
| PLACNOT02 | placenta, fetal F | 3 | 0.0495 |
| RATRNOT02 | heart, right atrium, 39 M | 2 | 0.0472 |
| BRAINOM02 | brain, 55 M, NORM, WM | 1 | 0.0454 |
| MELANOM01 | melanocytes, M, NORM, WM | 4 | 0.0431 |
| HUVENOB01 | HUVEC endothelial cell line, control | 1 | 0.0419 |
| THYRNOT03 | thyroid tumor, adenoma, 28 F | 1 | 0.0386 |
| OVARNOT03 | ovary, 43 F, match to OVARTUT01 | 1 | 0.0386 |
| THYMNOT02 | thymus, 3 M | 2 | 0.0386 |
| HNT2AGT01 | hNT-2 cell line, post-mitotic neurons | 2 | 0.0380 |
| PROSNOT07 | prostate, 69 M, match to PROSTUT05 | 1 | 0.0347 |
| SYNORAT03 | synovium, wrist, rheumatoid, 56 F | 2 | 0.0339 |
| LNODNOT02 | lymph nodes, 42 F | 1 | 0.0335 |
| TBLYNOT01 | T-B lymphoblast cell line, leukemia | 1 | 0.0326 |
| OVARTUT01 | ovarian tumor, 43 F, match to OVARNOT03 | 1 | 0.0323 |
| BSTMNON02 | brain stem, 72 M, NORM | 1 | 0.0319 |
| OVARNOT02 | ovary, 59 F | 1 | 0.0315 |
| BLADTUT02 | bladder tumor, carcinoma, 80 F | 1 | 0.0305 |
| LUNGTUT03 | lung tumor, carcinoma, 69 M | 1 | 0.0305 |
| CORPNOT02 | brain, corpus callosum, Alzheimer's, 74 M | 2 | 0.0302 |
| BRSTTUT02 | breast tumor, 54 F, match to BRSTNOT03 | 1 | 0.0298 |

Fig. 4B

| | | | |
|---|---|---|---|
| SYNORAT05 | synovium, knee, rheumatoid, 62 F | 1 | 0.0286 |
| LUNGNOT09 | lung, fetal M | 1 | 0.0285 |
| COLNFET02 | colon, fetal F | 2 | 0.0284 |
| PLACNOM02 | placenta, neonatal F, NORM, WM | 5 | 0.0278 |
| LUNGNOT12 | lung, 78 M | 1 | 0.0277 |
| BRAINOT09 | brain, fetal M | 1 | 0.0261 |
| LUNGNOT10 | lung, fetal M | 1 | 0.0261 |
| BRAITUT07 | brain tumor, left frontal, 32 M | 1 | 0.0258 |
| TLYMNOT02 | lymphocytes (non-adher PBMNC), M/F | 1 | 0.0254 |
| LUNGNOT02 | lung, 47 M | 1 | 0.0245 |
| MMLR1DT01 | macrophages (adher PBMNC), M/F, 24-hr MLR | 1 | 0.0236 |
| TMLR3DT01 | lymphocytes (non-adher PBMNC), M, 96-hr MLR | 1 | 0.0229 |
| PLACNOB01 | placenta, neonatal F | 1 | 0.0225 |
| CRBLNOT01 | brain, cerebellum, 69 M | 1 | 0.0195 |
| CERVNOT01 | cervix, 35 F | 1 | 0.0193 |
| ADENINB01 | adenoid, inflamed, 3y | 1 | 0.0190 |
| LUNGTUT02 | lung tumor, metastasis, 79 M, match to LUNGNOT03 | 1 | 0.0189 |
| SYNOOAT01 | synovium, knee, osteoarthritis, 82 F | 1 | 0.0179 |
| NEUTFMT01 | granulocytes, periph blood, M/F, treated fMLP | 1 | 0.0174 |
| UTRSNOT02 | uterus, 34 F | 1 | 0.0166 |
| PGANNOT01 | paraganglia, 46 M | 1 | 0.0160 |
| BRAITUT03 | brain tumor, astrocytoma, 17 F | 1 | 0.0153 |
| BRSTTUT03 | breast tumor, 58 F, match to BRSTNOT05 | 1 | 0.0148 |
| BRSTNOT03 | breast, 54 F, match to BRSTTUT02 | 1 | 0.0147 |
| LUNGFET03 | lung, fetal F | 1 | 0.0137 |
| LIVSFEM02 | liver/spleen, fetal M, NORM, WM | 4 | 0.0116 |
| BRAINOM01 | brain, infant F, NORM, WM | 2 | 0.0089 |

Fig. 4C

```
1   M D G Q K K - - - - - - - - - - - - - - - - - - - - - - - - - - - - - - - - - -               SEQ ID NO-1
1   M A E R X A A T Q - - - - - - - - - - - - - - - - - - - - - - - - - - - N W -               SEQ ID NO-3
1   M A A P G D P Q D E L L P L A G P G S Q W L R H R G E G E N E A V T P K G A T P             SEQ ID NO-5
1   M A A - - - - - - - - - - - - - - - - - - - - - - - - - - - - - - - - - - - -               SEQ ID NO-6
1   M Q A T A D S T K - - - - - - - - - - - - M D C V W S N W - - - - - - - - - -               SEQ ID NO-7
1   M - - - - - - - - - - - - - - - - - - - - - D C V W S N W - - - - - - - - - -               SEQ ID NO-8

9   - - - - - - - - - - - - - - - - - - - - - - - - - - - - - - - - - - - - - -                  SEQ ID NO-1
10  - - - - - - - - - - - - - - - - - - - - - - - - - - - - - - - - - - - - - -                  SEQ ID NO-3
41  A P Q A G E P S P G L G A R A R E A A S R E A G S G P A R Q S P V A M E T A S T              SEQ ID NO-5
4   - - - - - - - - - - - - - - - - - - - - - - - - - - - - - - - - - - - - - -                  SEQ ID NO-6
18  - - - - - - - - - - - - - - - - - - - - - - - - - - - - - - - - - - - - - -                  SEQ ID NO-7
9   - - - - - - - - - - - - - - - - - - - - - - - - - - - - - - - - - - - - - -                  SEQ ID NO-8

9   - - - - - - - - - - - - - - - - - - - - - - - - - - - - - - - - - - - - - -                  SEQ ID NO-1
10  - - - - - - - - - - - - - - - - - - - - - - - - - - - - - - - - - - - - - -                  SEQ ID NO-3
81  G V A G V S S A M D H T F S T T S K D G E G S C Y T S L I S D I C Y P P Q E D S              SEQ ID NO-5
4   - - - - - - - - - - - - - - - - - - - - - - - - - - - - - - - - - - - - - -                  SEQ ID NO-6
18  - - - - - - - - - - - - - - - - - - - - - - - - - - - - - - - - - - - - - -                  SEQ ID NO-7
9   - - - - - - - - - - - - - - - - - - - - - - - - - - - - - - - - - - - - - -                  SEQ ID NO-8

9   - - - - - - - - - - - - - - - - - - - - - - - - - - - - - - - - - - - - - -                  SEQ ID NO-1
10  - - - - - - - - - - - - - - - - - - - - - - - - - - - - - - - - - - - - - -                  SEQ ID NO-3
121 T Y F T G I L Q K E N G H V T I S E S P E E L G T P G P S L P D V P G I E S R G              SEQ ID NO-5
4   - - - - - - - - - - - - - - - - - - - - - - - - - - - - - - - - - - - - - -                  SEQ ID NO-6
18  - - - - - - - - - - - - - - - - - - - - - - - - - - - - - - - - - - - - - -                  SEQ ID NO-7
9   - - - - - - - - - - - - - - - - - - - - - - - - - - - - - - - - - - - - - -                  SEQ ID NO-8
```

Fig. 6A

```
  9  : ----------------------------------------  SEQ ID NO-1
 10  : ----------------------------------------  SEQ ID NO-3
161  : LFSSDSGIEMTPAESTEVNKILADPLDQMKAEAYKYIDIT   SEQ ID NO-5
  4  : ----------------------------------------  SEQ ID NO-6
 18  : ----------------------------------------  SEQ ID NO-7
  9  : ----------------------------------------  SEQ ID NO-8

9  : ----------------------------------------  SEQ ID NO-1
 10  : ----------------------------------------  SEQ ID NO-3
201  : RPEEVKHQEQHHPELEDKDLDFKNKDTDISIKPEGVREPD   SEQ ID NO-5
  4  : ----------------------------------------  SEQ ID NO-6
 18  : ----------------------------------------  SEQ ID NO-7
  9  : ----------------------------------------  SEQ ID NO-8

9  : ----------------------------------------  SEQ ID NO-1
 10  : ----------------------------------------  SEQ ID NO-3
241  : KPAPVEGKIIKDHLLEESTFAPYIDDLSEEQRRAPQITTP   SEQ ID NO-5
  4  : ----------------------------------------  SEQ ID NO-6
 18  : ----------------------------------------  SEQ ID NO-7
  9  : ----------------------------------------  SEQ ID NO-8

9  : ----------------------------------------  SEQ ID NO-1
 10  : ----------------------------------------  SEQ ID NO-3
281  : VKITLTEIEPSVETTQEKTPEKQDICLKPSPDTVPTVTV    SEQ ID NO-5
  4  : ----------------------------------------  SEQ ID NO-6
 18  : ----------------------------------------  SEQ ID NO-7
  9  : ----------------------------------------  SEQ ID NO-8
```

```
  9                                                                              SEQ ID NO-1
 10  - - - - - - - - - - - - - - - - - - - - - - - - - - - - - - - - - - - -    SEQ ID NO-3
321  S E P E D D S P G S I T P P S S G T E P S A A E S Q G K G S I S E D E L I T A I  SEQ ID NO-5
  4  - - - - - - - - - - - - - - - - - - - - - - - - - - - - - - - - - - - -    SEQ ID NO-6
 18  - - - - - - - - - - - - - - - - - - - - - - - - - - - - - - - - - - - -    SEQ ID NO-7
  9  - - - - - - - - - - - - - - - - - - - - - - - - - - - - - - - - - - - -    SEQ ID NO-8

9                                                                              SEQ ID NO-1
 26  - - - - - - - - - - - - - - - - - - - - - - - - - - - - - - - - - - - -    SEQ ID NO-3
361  K E A K G L S Y E T A E N P R P V G Q L A D R P E V K A R S G P P T I P S P L D  SEQ ID NO-5
  4  - - - - - - - - - - - - - - - - - - - - - - - - - - - - - - - - - - - -    SEQ ID NO-6
 18  - - - - - - - - - - - - - - - - - - - - - - - - - - - - - - - - - - - -    SEQ ID NO-7
  9  - - - - - - - - - - - - - - - - - - - - - - - - - - - - - - - - - - - -    SEQ ID NO-8

9                                                                              SEQ ID NO-1
 26  - - - - - - - - - - - - - - - - - - - - - - - - G G G G S P                 SEQ ID NO-3
401  H E A S S A E S G D S E I E L V S E D P M A A E D A L P S G Y V S F G H V G G P  SEQ ID NO-5
  4  - - - - - - - - - - - - - E D A L P S G Y V S F G H V G G P                 SEQ ID NO-6
 18  - - - - - - - - - - - - - - - - - - - - - - - - - - - - - - - - - - - -    SEQ ID NO-7
  9  - - - - - - - - - - - - - - - - - - - - - - - - - - - - - - - - - - - -    SEQ ID NO-8

9                                                                              SEQ ID NO-1
 32  - - G A C P A - - - - - - - - - - - - - - - - - - - - - - - - S C A V H -   SEQ ID NO-3
441  P P S P A S P S I Q Y S I L R E E R E A E L D S E L I I E S C D A S S E E S  SEQ ID NO-5
 21  P P S P A S P S I Q Y S I L R E E R E A E L D S E L I I E S C D A S S E E S  SEQ ID NO-6
 18  - - - - - - - - - - - - - - - - - - - - L G T K S C S S - - - - - - - - -   SEQ ID NO-7
  9  - - - - - - - - - - - - - - - - - - - - - - - - - - - - - - - - - - - -    SEQ ID NO-8
```

Fig. 6D

```
 64  Y K G V I Q A I Q K S D E G H P F R A Y L E S E V A I S E E L V Q K Y S N S A L   SEQ ID NO-1
100  Y K S V I Q A V Q K S E E G H P F K A Y L D S E V D I T L S S E A F H N Y M N A A M SEQ ID NO-3
641  Y K S V L Q A V Q K T D E G H P F K A Y L E L E I T L S Q E Q I Q K Y T D C L Q   SEQ ID NO-5
221  Y K S V L Q A V Q K T D E G H P F K A Y L E L E I T L S Q E Q I Q K Y T D C L Q   SEQ ID NO-6
 73  Y K S V L Q A V Q K T D E G H P F K A Y L E L E I T L S Q E Q I Q K Y T D C L Q   SEQ ID NO-7
 64  Y K S V L Q A V Q K T D E G H P F K A Y L E L E I T L S Q E Q I Q K Y T D C L Q   SEQ ID NO-8

104  G H V N C T I K E L R R L F L V D D L V D S L K F A V L M W V F T Y V G A L F N   SEQ ID NO-1
140  V H I N R A L K L I I R L F L V E D L V D S L K L A V F M W L M T Y V V G A V F N SEQ ID NO-3
681  F Y V N S T L K E L R R L F L V Q D L V D S L K F A V L M W L L T Y V V G A L F N SEQ ID NO-5
261  F Y V N S T L K E L R R L F L V Q D L V D S L K F A V L M W L L T Y V V G A L F N SEQ ID NO-6
113  F Y V N S T L K E L R R L F L V Q D L V D S L K F A V L M W L L T Y V V G A L F N SEQ ID NO-7
104  L Y V N S T L K E L R R L F L V Q D L V D S L K F A V L M W L L T Y V V G A L F N SEQ ID NO-8

144  G L T L I L A L I S L F S V P V I Y E R H Q A Q I D H Y L G L A N K N V K D A     SEQ ID NO-1
180  G I T L L I L A E L L I X S V P I V Y X K Y - - - - - - - - - - - - - - L         SEQ ID NO-3
721  G L T L L L M A V V S M F T L P V V Y V K H Q A Q I D Q Y L G L V R T H I N A V   SEQ ID NO-5
301  G L T L L L M A V V S M F T L P V V Y V K H Q A Q I D Q Y L G L V R T H I N A V   SEQ ID NO-6
153  G L T L L L M A V V S M F T L P V V Y V K H Q A Q I D Q Y L G L V R T H I N A V   SEQ ID NO-7
144  G L T L L L M A V V S M F T L P V V Y V K H Q A Q V D Q Y L G L V R T H I N T V   SEQ ID NO-8

184  M A K I Q A K I P - - G - - - - - - - - - - - - - - - - - - - - - - - - - -       SEQ ID NO-1
202  - - K V P S K T P W N R Q K K G R I S T W - - - - - - - - - - - - - - - - -       SEQ ID NO-3
761  V A K I Q A K I P - - G A K - - - - K P E M Q Q - - - - - - - - - - - - - -       SEQ ID NO-5
341  V A K I Q A K I P - - G A K - - - - - - - - - - - - - - - - - - - - - - - -       SEQ ID NO-6
193  V A K I Q A K I P - - G A K - - - - - - - - - - - - - - - - - - - - - - - -       SEQ ID NO-7
184  V A K I Q A K I P - - G A R G M L S R W L P Q E K P D M N G G V W S G N S S L   SEQ ID NO-8
```

Fig. 6E

```
194  L K R K A E
228  L K H L I V I T S L - - - - - - - - - -                                    SEQ ID NO-1
773  - - R H A E                                                                 SEQ ID NO-3
353  - - R H A E                                                                 SEQ ID NO-5
205  - - R H A E                                                                 SEQ ID NO-6
221  L P R Y C E L I V S L P Q Y H N L R G K L R D R C F Q S F P V L L G Y L S P P R   SEQ ID NO-7
                                                                                 SEQ ID NO-8

199                                                                              SEQ ID NO-1
241                                                          - L V L             SEQ ID NO-3
776                                                                              SEQ ID NO-5
356                                                                              SEQ ID NO-6
208                                                                              SEQ ID NO-7
261  P L S S T K V                                                               SEQ ID NO-8
```

Fig. 6F

POLYNUCLEOTIDES ENCODING TWO NOVEL HUMAN NEUROENDOCRINE-SPECIFIC PROTEINS

FIELD OF THE INVENTION

The present invention relates to nucleic acid and amino acid sequences of two novel human NSP-like proteins and to the use of these sequences in the diagnosis, study, prevention and treatment of disease.

BACKGROUND OF THE INVENTION

Neuroendocrine-specific proteins (NSP-A, NSP-B, and NSP-C) are a recently characterized group of membrane-anchored endoplasmic reticulum (ER) proteins that share identical carboxy-terminal amino acid sequences (van de Velde H J et al (1994) J Cell Sci 107: 2403–2416). Evidence suggests that NSP-A and NSP-C expression is restricted to neuronal and endocrine cell populations (van de Velde, supra). Immunohistochemical studies showed that rat NSP-A is expressed throughout the rat brain (van de Velde H J et al (1994) Mol Brain Res 23: 81–92). NSP-H, however, is found only in a small cell lung carcinoma cell line and probably represents an aberrant NSP gene product (Roebroek A J et al (1993) J Biol Chem 268: 13439–13447). A previously reported neuronally expressed rat gene, CI-13, and two partially sequenced human cDNAs (GI 391043 and GI 894620), have a high degree of homology to NSPs which suggests that NSPs belong to a larger family of proteins (Wieczorek D F et al (1991) Mol Brain Res 10: 33–41; Bell G I et al (1993) Hum Mol Genet 2: 1793–798; Martin-Galla A et al (1992) Nat Genet 1: 34–39).

Two large hydrophobic regions characterize the NSPs and homologous proteins and suggest membrane association. In fact, immunofluorescence and biochemical studies have established an association between NSPs and membranes of the ER (Senden N H et al (1994) Eur J Cell Biol 65: 341–353). Analysis of NSP-A deletion mutants indicates that the carboxy-terminal hydrophobic region is necessary for membrane binding (van de Velde et al, supra). Carboxy-terminal amino acid sequences of the NSPs are highly homologous, although they are not a perfect match to a consensus motif sufficient for retention of transmembrane proteins in the ER (van de Velde, supra; Jackson M R et al (1993) J Cell Biol 121: 317–333). Thus, it appears likely that NSPs and related proteins are targeted to the ER by conserved carboxy-terminal amino acids.

Immunostaining with anti-NSP-A antibodies suggests that NSP-A may be associated with both the rough and smooth neuronal ER. On the basis of this evidence and knowledge of neuronal ER function, van de Velde et al (1994; supra) conclude that NSPs may be involved in the protein transport process or in the regulation of intracellular calcium levels in neuronal cells.

NSP-like Proteins and Disease

Dysfunction of ER-mediated neuronal protein transport may contribute to neurodegenerative diseases. For example, in amyotrophic lateral sclerosis (ALS), a degenerative disease of motor neurons, deposition of neurofilaments in neuronal axons leads to dramatic defects in ER-mediated axonal transport of a variety of proteins (Collard J F et al (1995) Nature 375: 61–64). Defects in protein transport have been further implicated in the pathogenesis of ALS by a transgenic mouse study in which ALS is modeled by a mutation in superoxide dismutase (SOD). SOD mutant animals displayed clinical and pathological features of human ALS and showed axonal transport defects associated with dilation of the ER (Mourelatos Z et al (1996) Proc Natl Acad Sci 93: 5472–5477).

Analysis of specimens of a wide variety of primary human tumors show that NSP-A and NSP-C are expressed in small cell lung carcinoma, carcinoid tumors of the lung, but not in non-neuroendocrine non-small cell lung carcinomas (van de Velde et al (1994) Cancer Res 54: 4769–4776). Furthermore, antibodies generated to small-cell lung carcinoma surface antigens recognize NSP-A, NSP-B, and NSP-C. Therefore, NSPs may act as markers in human lung cancer diagnosis and provide an avenue for corrective treatment (Senden N H et al (1994) Int J Cancer Suppl 8: 84–88).

New NSP-like proteins could satisfy a need in the art by providing new means of diagnosing and treating cancer and neurodegenerative disorders such as ALS.

SUMMARY

The present invention discloses two novel human NSP-like proteins (hereinafter referred to individually as NSPLPA and NSPLPB, and collectively as NSPLP), characterized as having homology to human NSP-A (GI 307307), NSP-B (GI 307309), NSP-C (GI 307311), and rat CI-13 (GI 281046). Accordingly, the invention features two substantially purified NSP-like proteins, as shown in amino acid sequence of SEQ ID NO:1 and SEQ ID NO:3, and having characteristics of NSPs.

One aspect of the invention features isolated and substantially purified polynucleotides which encode NSPLP. In a particular aspect, the polynucleotide is the nucleotide sequence of SEQ ID NO:2 or SEQ ID NO:4. In addition, the invention features polynucleotide sequences that hybridize under stringent conditions to SEQ ID NO:2 or SEQ ID NO:4.

The invention further relates to nucleic acid sequences encoding NSPLP, oligonucleotides, peptide nucleic acids (PNA), fragments, portions or antisense molecules thereof, and expression vectors and host cells comprising polynucleotides which encode NSPLP. The present invention also relates to antibodies which bind specifically to NSPLP, pharmaceutical compositions comprising substantially purified NSPLP, fragments thereof, or antagonists of NSPLP, in conjunction with a suitable pharmaceutical carrier, and methods for producing NSPLP, fragments thereof, or antagonists of NSPLP.

BRIEF DESCRIPTION OF THE FIGURES

FIGS. 1A, 1B, and 1C show the amino acid sequence (SEQ ID NO:1) and nucleic acid sequence (SEQ ID NO:2) of the novel NSP-like protein, NSPLPA. The alignment was produced using MacDNAsis software (Hitachi Software Engineering Co Ltd).

FIGS. 2A, 2B, and 2C show the amino acid sequence (SEQ ID NO:3) and nucleic acid sequence (SEQ ID NO:4) of the novel NSP-like protein, NSPLPB (MacDNAsis software, Hitachi Software Engineering Co Ltd).

FIGS. 3A, 3B, 3C, 3D, and 3E show the northern analysis for the consensus sequence (SEQ ID NO:4). The northern analysis was produced electronically using LIFESEQ™ database (Incyte Pharmaceuticals, Palo Alto Calif.).

FIGS. 4A, 4B, and 4C show the northern analysis for Incyte Clones 31870 (SEQ ID NO:2) (LIFESEQ™ database, Incyte Pharmaceuticals, Palo Alto Calif.).

Figure 6D:
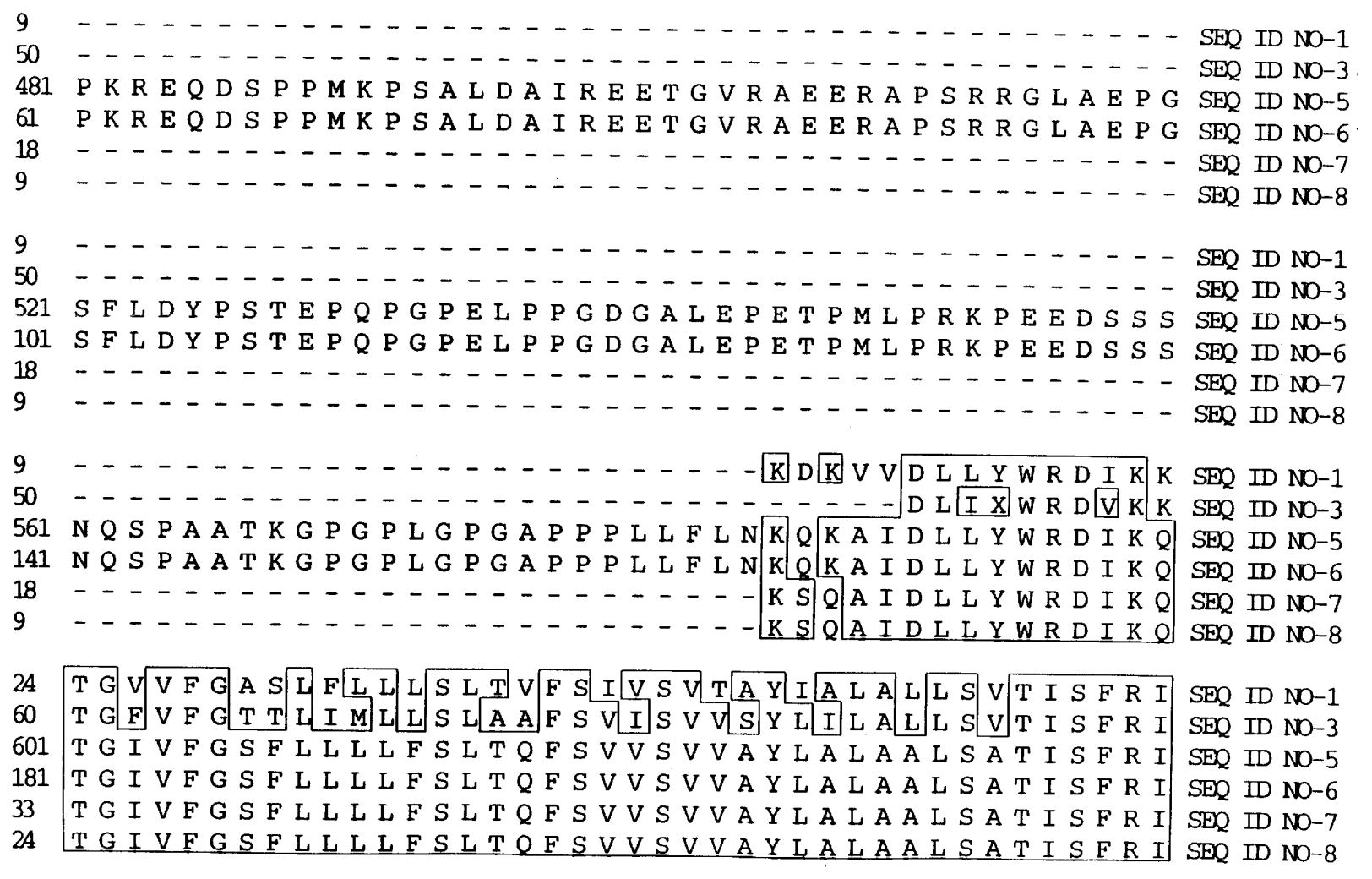

FIGS. 6A, 6B, 6C, 6D, 6E and 6F show the amino acid sequence alignments among NSPLPA (SEQ ID NO:1), NSPLPB (SEQ ID NO:3), NSP-A (GI 307307; SEQ ID NO:5), NSP-B (GI 307309; SEQ ID NO:6), NSP-C (GI 307311); SEQ ID NO:7), and rat CI-13 (GI 281046 SEQ ID NO:8) produced using the multisequence alignment program of DNAStar software (DNAStar Inc, Madison Wis.).

DETAILED DESCRIPTION OF THE INVENTION

Definitions

Figure 5:
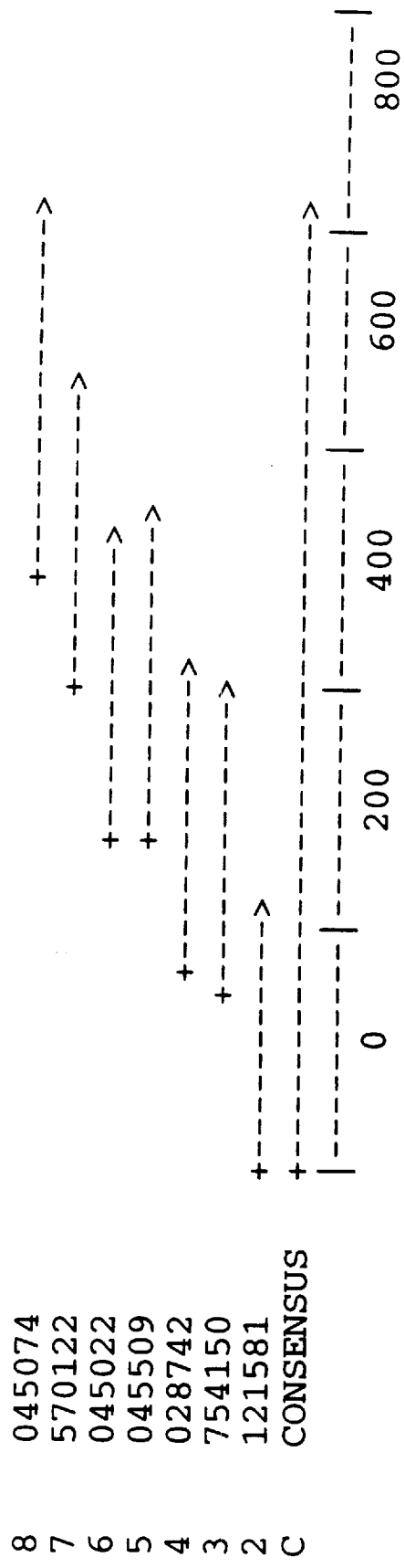
FIG. 5 shows the assembly for the consensus sequence (SEQ ID NO:2).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, NSPLP refers to the amino acid sequences of substantially purified NSPLP obtained from any species, particularly mammalian, including bovine, ovine, porcine, murine, equine, and preferably human, from any source whether natural, synthetic, semi-synthetic or recombinant.

A "variant" of NSPLP is defined as an amino acid sequence that is altered by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring NSPLP.

A "substitution" results from the replacement of one or more amino acids or nucleotides by different amino acids or nucleotides, respectively.

The term "biologically active" refers to a NSPLP having structural, regulatory or biochemical functions of a naturally occurring NSPLP. Likewise, "immunologically active" defines the capability of the natural, recombinant or synthetic NSPLP, or any oligopeptide thereof, to induce a specific immune response in appropriate animals or cells and to bind with specific antibodies.

The term "derivative" as used herein refers to the chemical modification of a nucleic acid encoding NSPLP or the encoded NSPLP. Illustrative of such modifications would be replacement of hydrogen by an alkyl, acyl, or amino group. A nucleic acid derivative would encode a polypeptide which retains essential biological characteristics of natural NSPLP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

Preferred Embodiments

The present invention relates to novel NSPLP and to the use of the nucleic acid and amino acid sequences in the study, diagnosis, prevention and treatment of disease. cDNAs encoding a portion of NSPLP were found in neuronal and endocrine tissue-derived cDNA libraries and in a variety of other tissues, including many types of tumors (FIGS. 3A–C, 4A, and 4B).

The present invention also encompasses NSPLP variants. A preferred NSPLP variant is one having at least 80% amino acid sequence similarity to the NSPLP amino acid sequence (SEQ ID NO:1), a more preferred NSPLP variant is one having at least 90% amino acid sequence similarity to SEQ ID NO:1 and a most preferred NSPLP variant is one having at least 95% amino acid sequence similarity to SEQ ID NO:1.

Nucleic acids encoding the human NSPLP of the present invention were first identified in cDNA, Incyte Clones 31870 (SEQ ID NO:4; THP-1 cell cDNA library, THP1NOB01) and 28742 (SEQ ID NO:9; fetal spleen CDNA library, SPLNFET01), through a computer-generated search for amino acid sequence alignments. A consensus sequence, SEQ ID NO:2, was derived from the following overlapping nucleic acid sequences: Incyte Clones 28742 (from cDNA library SPLNFET01); 45022, 45074, and 45509 (CORNNOT01); 121581 (MUSCNOT01); 570122 (MMLR3DT01); and 754150 (BPATUT02; FIG. 5). The nucleic acid sequence of SEQ ID NO:2 encodes the NSPLPA amino acid sequence, SEQ ID NO:1. The nucleic acid sequence of SEQ ID NO:4 encodes the NSPLPB amino acid sequence, SEQ ID NO:3. The nucleic acid sequence of SEQ ID NO:4 from residue $C_{496}$ to $T_{708}$ has 97% identity to the partial cDNA sequence of clone hbc043 (GI 39104; Bell et al, supra).

Figure 7:
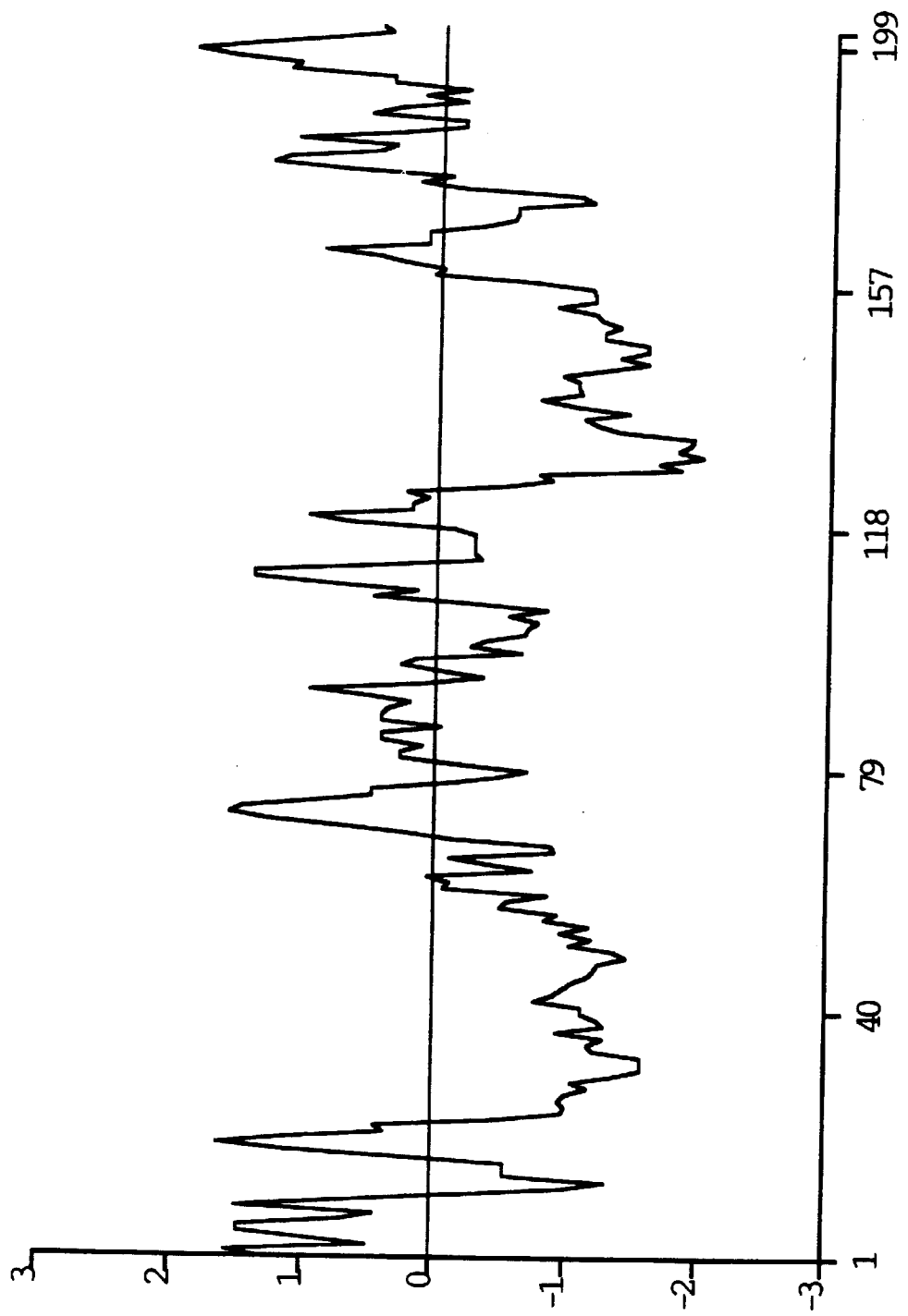
FIG. 7 shows the hydrophobicity plot (generated using MacDNAsis software) for NSPLPA, SEQ ID NO:1; the X axis reflects amino acid position, and the negative Y axis, hydrophobicity (FIGS. 7, 8, and 9).
Figure 8:
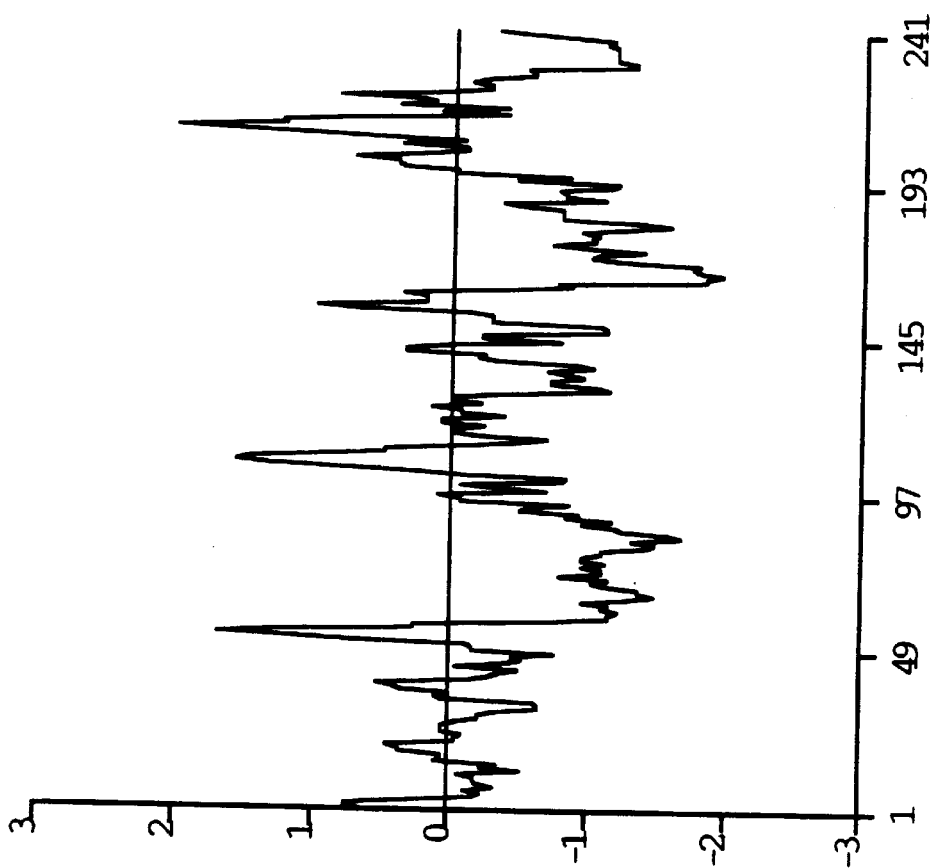
FIG. 8 shows the hydrophobicity plot for NSPLPB, SEQ ID NO:3.
Figure 9:
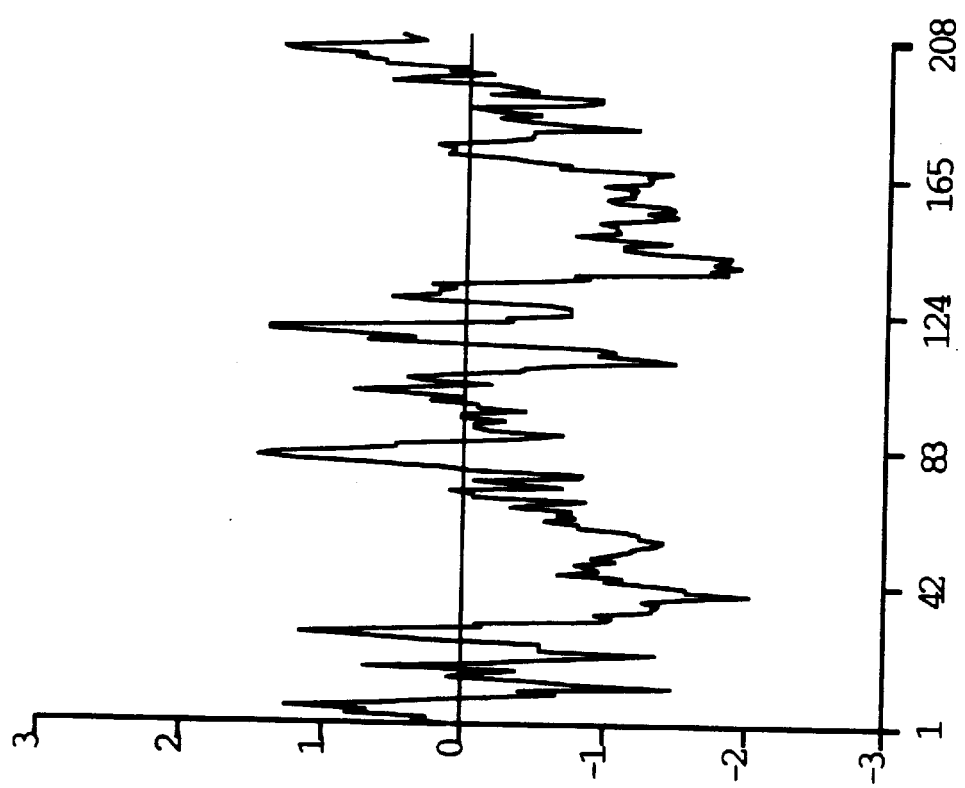
FIG. 9 shows the hydrophobicity plot for NSP-C, SEQ ID NO:7.

The present invention is based, in part, on the chemical and structural homology among NSPLPA, NSPLPB, NSP-A (GI 307307; Roebroek et al, supra), NSP-B (GI 307309; Roebroek et al, supra), NSP-C (GI 307311; Roebroek et al, supra), and rat CI-13 (GI 281046; Wieczorek et al, supra; FIGS. 6A–D). NSPLPA and NSP-C share 66% identity, NSPLPB and NSP-C share 48% identity, while NSPLPA and NSPLPB share 50% identity. As illustrated by FIGS. 7, 8, and 9, NSPLPA, NSPLPB, and NSP-C have similar hydrophobicity plots suggesting similar structure. Like the NSPs, NSPLPA and NSPLPB have two large hydrophobic regions that could be used for membrane attachment. The carboxy-terminal amino acids $Lys_{195}$ through $Lys_{197}$ of NSPLPA precisely match, in position as well as sequence, an ER retention motif defined by Jackson et al (1993; supra). The novel NSPLPA is 199 amino acids long and has one potential N glycosylation site. The novel NSPLPB is 241 amino acids long.

The NSPLP Coding Sequences

The nucleic acid and deduced amino acid sequences of NSPLP are shown in FIGS. 1A, 1B, 1C, 2A, 2B, and 2C. In accordance with the invention, any nucleic acid sequence which encodes the amino acid sequence of NSPLP can be used to generate recombinant molecules which express NSPLP. In a specific embodiment described herein, a nucleotide sequence encoding a portion of NSPLP was first isolated as Incyte Clones 31870 from a THP-1 cell cDNA library (THP1NOB01). While, Incyte Clone 28742 was first isolated from a fetal spleen cDNA library (SPLNFET01).

It will be appreciated by those Skilled in the art that as a result of the degeneracy of the genetic code, a multitude of NSPLP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring NSPLP, and all such variations are to be considered as being specifically disclosed.

Although nucleotide sequences which encode NSPLP and its variants are preferably capable of hybridizing to the nucleotide sequence of the naturally occurring NSPLP under appropriately selected conditions of stringency, it may be advantageous to produce nucleotide sequences encoding NSPLP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding NSPLP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a NSPLP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding NSPLP or any portion thereof.

Also included within the scope of the present invention are polynucleotide sequences that are capable of hybridizing to the nucleotide sequences of FIGS. 1A, 1B, 1C, 2A, 2B, and 2C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined stringency.

Altered nucleic acid sequences encoding NSPLP which may be used in accordance with the invention include deletions, insertions or substitutions of different nucleotides resulting in a polynucleotide that encodes the same or a functionally equivalent NSPLP. The protein may also show deletions, insertions or substitutions of amino acid residues which produce a silent change and result in a functionally equivalent NSPLP. Deliberate amino acid substitutions may be made on the basis of similarity in polarity, charge, solubility, hydrophobicity, hydrophilicity, and/or the amphipathic nature of the residues as long as the biological activity of NSPLP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of NSPLP. As used herein, an "allele" or "allelic sequence" is an alternative form of NSPLP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (U.S. Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding NSPLP may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to at known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PromoterFinder libraries to walk in genomic DNA (PromoterFinder™ Clontech (Palo Alto Calif.). This process avoids the need to screen libraries and is useful in finding intron/exon junctions.

Preferred libraries for screening for full length cDNAs are ones that have been size-selected to include larger cDNAs. Also, random prime libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eq. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–2858).

Expression of the Nucleotide Sequence

In accordance with the present invention, polynucleotide sequences which encode NSPLP, fragments of the polypeptide, fusion proteins or functional equivalents thereof may be used in recombinant DNA molecules that direct the expression of NSPLP in appropriate host cells. Due to the inherent degeneracy of the genetic code, other DNA sequences which encode substantially the same or a functionally equivalent amino acid sequence, may be used to clone and express NSPLP. As will be understood by those of skill in the art, it may be advantageous to produce NSPLP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of NSPLP expression or to produce recombinant RNA transcripts having desirable properties, such as a longer half-life, than transcripts produced from naturally occurring sequence.

The nucleotide sequences of the present invention can be engineered in order to alter a NSPLP coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotides encoding NSPLP may be ligated to a heterologous sequence to encode a fusion protein. For example, for screening of peptide libraries for inhibitors of NSPLP activity, it may be useful to encode a chimeric NSPLP protein that is recognized by a commercially available antibody. A fusion protein may also be engineered to contain a cleavage site located between a NSPLP sequence and the heterologous protein sequence, so that the NSPLP may be cleaved and purified away from the heterologous moiety.

In an alternate embodiment of the invention, the coding sequence of NSPLP may be synthesized, whole or in part, using chemical methods well known in the art (see Caruthers M H et cl (1980) Nuc Acids Res Symp Ser 215–23, Horn T et al(1980) Nuc Acids Res Symp Ser 225–32, etc). Alternatively, the protein itself could be produced using chemical methods to synthesize a NSPLP amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of NSPLP, or any part thereof, may be altered during direct synthesis and/or combined using chemical methods with sequences from other proteins, or any part thereof, to produce a variant polypeptide.

In order to express a biologically active NSPLP, the nucleotide sequence encoding NSPLP or its functional equivalent, is inserted into an appropriate expression vector, ie, a vector which contains the necessary elements for the transcription and translation of the inserted coding sequence.

Methods which are well known to those skilled in the art can be used to construct expression vectors containing a NSPLP coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a NSPLP coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of NSPLP, vectors based on SV40 or EBV may be used with an appropriate selectable marker.

In bacterial systems, a number of expression vectors may be selected depending upon the use intended for NSPLP. For example, when large quantities of NSPLP are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the NSPLP coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding NSPLP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express NSPLP is an insect system. In one such system, *Autographa californica* nuclear polyhedrosis virus (AcNPV) is used as a vector to express foreign genes in *Spodontera frugiperda* cells or in Trichoplusia larvae. The NSPLP coding sequence may be cloned into a nonessential region of the virus, such as the polyhedrin gene, and placed under control of the polyhedrin promoter. Successful insertion of NSPLP will render the polyhedrin gene inactive and produce recombinant virus lacking coat protein coat. The recombinant viruses are then used to infect *S. frugiperda* cells or Trichoplusia larvae in which NSPLP is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a NSPLP coding sequence may be ligated into an adenovirus transcription/translation complex consisting of the late promoter and tripartite leader sequence. Insertion in a nonessential E1 or E3 region of the viral genome will result in a viable virus capable of expressing NSPLP in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a NSPLP sequence. These signals include the ATG initiation codon and adjacent sequences. In cases where NSPLP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express NSPLP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the NSPLP is inserted within a marker gene sequence, recombinant cells containing NSPLP can be identified by the absence of marker gene function. Alternatively, a marker gene can be placed in tandem with a NSPLP sequence under the control of a single promoter. Expression of the marker gene in response to induction or selection usually indicates expression of the tandem NSPLP as well.

Alternatively, host cells which contain the coding sequence for NSPLP and express NSPLP may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding NSPLP can be detected by DNA-DNA or DNA-RNA hybridization or amplification using probes, portions or fragments of polynucleotides encoding NSPLP. Nucleic acid amplification based assays involve the use of oligonucleotides or oligomers based on the NSPLP-encoding sequence to detect transformants containing DNA or RNA encoding NSPLP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of NSPLP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NSPLP is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding NSPLP include oligolabeling, nick translation, end-labeling or PCR amplification using a labeled nucleotide. Alternatively, the NSPLP sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of NSPLP

Host cells transformed with a nucleotide sequence encoding NSPLP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding NSPLP can be designed with signal sequences which direct secretion of NSPLP through a prokaryotic or eukaryotic cell membrane. Other recombinant constructions may join NSPLP to nucleotide sequence encoding a polypeptide domain which will facilitate purification of soluble proteins (Kroll D J et al (1993) DNA Cell Biol 12:441–53; of discussion of vectors infra containing fusion proteins).

NSPLP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and NSPLP is useful to facilitate purification. One such expression vector provides for expression of a fusion protein compromising an NSPLP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying NSPLP from the fusion protein.

In addition to recombinant production, fragments of NSPLP may be produced by direct peptide synthesis using solid-phase techniques (of Stewart et al (1969) *Solid-Phase Peptide Synthesis*, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of NSPLP may be chemically synthesized separately and combined using chemical methods to produce the full length molecule.

Uses of NSPLP

The rationale for use of the nucleotide and polypeptide sequences disclosed herein is based in part on the chemical and structural homology among the novel NSPLP proteins disclosed herein, NSP-A (GI 307307; Roebroek et al, supra), NSP-B (GI 307309; Roebroek et al, supra), NSP-C (GI 307311; Roebroek et al, supra), and rat CI-13 (GI 281046; Wieczorek et al, supra).

Accordingly, NSPLP or a NSPLP derivative may be used to treat cancer and neurodegenerative disorders, such as ALS. In those conditions where NSPLP protein activity is not desirable, cells could be transfected with antisense sequences of NSPLP-encoding polynucleotides or provided with antagonists of NSPLP.

NSPLP Antibodies

NSPLP-specific antibodies are useful for the diagnosis of conditions and diseases associated with expression of NSPLP. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

NSPLP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the en-ire amino acid sequence of a small, naturally occurring molecule. Short stretches of NSPLP amino acids may be fused with those of another protein such as keyhole limpet hemocyanin and antibody produced against the chimeric molecule. Procedures well known in the art can be used for the production of antibodies to NSPLP.

For the production of antibodies, various hosts including goats, rabbits, rats, mice, etc may be immunized by injection with NSPLP or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium paryum* are potentially useful human adjuvants.

Monoclonal antibodies to NSPLP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce NSPLP-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for NSPLP may also be generated. For example, such fragments include, but are not limited to, the F(ab')2 fragments which can be produced by pepsin digestion of the antibody molecule and the Fab fragment, which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between NSPLP and its specific antibody and the measurement of complex formation. A two-site, monoclonal-based immunoassay utilizing monoclonal antibodies reactive to two noninterfering epitopes on a specific NSPLP protein is preferred, but a competitive binding assay may also be employed. These assays are described in Maddox DE et al (1983, J Exp Med 158:1211).

Diagnostic Assays Using NSPLP Specific Antibodies

Particular NSPLP antibodies are useful for the diagnosis of conditions or diseases characterized by expression of NSPLP or in assays to monitor patients being treated with NSPLP, agonists or inhibitors. Diagnostic assays for NSPLP include methods utilizing the antibody and a label to detect NSPLP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring NSPLP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on NSPLP is preferred, but a competitive binding assay may be employed. These assays are described, among other places, in Maddox, D E et al (1983, J Exp Med 158:1211).

In order to provide a basis for diagnosis, normal or standard values for NSPLP expression must be established. This is accomplished by combining body fluids or cell extracts taken from normal subjects, either animal or human, with antibody to NSPLP under conditions suitable for complex formation which are well known in the art. The amount of standard complex formation may be quantified by comparing various artificial membranes containing known quantities of NSPLP with both control and disease samples from biopsied tissues. Then, standard values obtained from normal samples may be compared with values obtained from samples from subjects potentially affected by disease. Deviation between standard and subject values establishes the presence of disease state.

Drug Screening

NSPLP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between NSPLP and the agent being tested, may be measured.

Another technique for drug screening which may be used provides for high throughput screening of compounds having suitable binding affinity to the NSPLP is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of NSPLP and washed. Bound NSPLP is then detected by methods well known in the art. Purified NSPLP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding NSPLP specifically compete with a test compound for binding NSPLP. In this manner, the antibodies can be used to detect the presence of any peptide which shares one or more antigenic determinants with NSPLP.

Uses of the Polynucleotide Encoding NSPLP

A polynucleotide encoding NSPLP, or any part thereof, may be used for diagnostic and/or therapeutic purposes. For diagnostic purposes, polynucleotides encoding NSPLP of this invention may be used to detect and quantitate gene expression in biopsied tissues in which expression of NSPLP may be implicated. The diagnostic assay is useful to distinguish between absence, presence, and excess expression of NSPLP and to monitor regulation of NSPLP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding NSPLP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding NSPLP, alleles or related sequences.

Probes may also be used for the detection of related sequences and should preferably contain at least 50% of the nucleotides from any of these NSPLP encoding sequences.

The hybridization probes of the subject invention may be derived from the nucleotide sequence of SEQ ID NO:2 or from genomic sequence including promoter, enhancer elements and introns of the naturally occurring NSPLP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding NSPLP include the cloning of nucleic acid sequences encoding NSPLP or NSPLP derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding NSPLP may be used for the diagnosis of conditions or diseases with which the expression of NSPLP is associated. For example, polynucleotide sequences encoding NSPLP may be used in hybridization or PCR assays of fluids or tissues from biopsies to detect NSPLP expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding NSPLP disclosed herein provide the basis for assays that detect activation or induction associated with cancer and neurodegenerative disorders, such as ALS. The nucleotide sequence encoding NSPLP may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding NSPLP in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for NSPLP expression must be established. This is accomplished by combining body fluids or cell extracts taken from normal subjects, either animal or human, with NSPLP, or a portion thereof, under conditions suitable for hybridization or amplification. Standard hybridization may be quantified by comparing the values obtained for normal subjects with a dilution series of NSPLP run in the same experiment where a known amount of a substantially purified NSPLP is used. Standard values obtained from normal samples may be compared with values obtained from samples from patients afflicted with NSPLP-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the NSPLP sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabelled (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of NSPLP in extracts of biopsied tissues may indicate the onset of cancer. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to genes encoding NSP-like proteins and its expression profile, polynucleotide sequences encoding NSPLP disclosed herein may be useful in the treatment of conditions such as cancer and neurodegenerative disorders, such as ALS.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding NSPLP. See, for example, the techniques described in Sambrook et al (supra) and Ausubel et al (supra).

The polynucleotides comprising full length cDNA sequence and/or its regulatory elements enable researchers to use sequences encoding NSPLP as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding NSPLP can be turned off by transfecting a cell or tissue with expression vectors which express high levels of a desired NSPLP-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding NSPLP, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding NSPLP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding NSPLP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for NSPLP disclosed herein may be used in molecular biology techniques that have not yet been developed, provided the new techniques rely on properties of nucleotide sequences that are currently known, including but not -Limited to such properties as the triplet genetic code and specific base pair interactions.

Detection and Mapping of Related Polynucleotide Sequences

The nucleic acid sequence for NSPLP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome CDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding NSPLP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example a sequence tagged site based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically Duffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of NSPLP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, logs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that NSPLP or an NSPLP derivative can be delivered in a suitable formulation to block the progression of cancerous cell growth or of neuronal degeneration. Similarly, administration of NSPLP antagonists may also inhibit the activity or shorten the lifespan of this protein.

The examples below are provided to illustrate the subject invention and are not included for the purpose of limiting the invention.

EXAMPLES

I Construction of CDNA Libraries

THP-1

THP-1 is a human leukemic cell line derived from the blood of a 1-year-old boy with acute monocytic leukemia. The THP-1 cells represent monocytes. The THP-1 cDNA library was custom constructed by Stratagene (Stratagene, 11099 M. Torrey Pines Rd., La Jolla, Calif. 92037) essentially as described below.

Stratagene prepared the CDNA library using oligo d(T) priming. Synthetic adapter oligonucleotides were ligated onto the cDNA molecules enabling them to be inserted into the Uni-ZAP™ vector system (Stratagene). This allowed high efficiency unidirectional (sense orientation) lambda library construction and the convenience of a plasmid system with blue/white color selection to detect clones with CDNA insertions.

The quality of the cDNA library was screened using DNA probes, and then, the pBluescript® phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom-constructed library phage particles were infected into E. coli host strain XL1-Blue® (Stratagene). The high transformation efficiency of this bacterial strain increases the probability that the cDNA library will contain rare, underrepresented clones. Alternative unidirectional vectors include, but are not limited to, pcDNAI (Invitrogen, San Diego Calif.) and pSHlox-1 (Novagen, Madison Wis.).

Fetal spleen

The human spleen cell cDNA library was custom constructed by Stratagene (catalogue #937205, Stratagene, La Jolla Calif.). The starting cell population is mixed, having been obtained from fetal spleens which have a diverse cell population. Furthermore, the fetal spleens have been pooled from different sources. Poly(A+) RNA (mRNA) was purified from the spleen cells. cDNA was synthesized from the mRNA. Synthetic adaptor oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions. Alternative unidirectional vectors are pcDNA1 (Invitrogen, San Diego Calif.) and pSHlox-1 (Novagen, Madison Wis.).

II Isolation of cDNA Clones

THP-1

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pbluescript phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

An alternate method of purifying phagemid has recently become available. It utilizes the Miniprep Kit (Catalog No. 77468, available from Advanced Genetic Technologies Corp., 19212 Orbit Drive, Gaithersburg, Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 μl of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

Phagemid DNA was also purified using the QIAWELL-8 Plasmid Purification System from the QIAGEN® DNA Purification System (QIAGEN Inc, Chatsworth Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations.

Fetal spleen

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was also purified using the QIAWELL-8 Plasmid Purification System from the QIAGEN® DNA Purification System (QIAGEN Inc, Chatsworth Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entice database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of NSPLP-Encoding Polynucleotides to Full Length or to Recover Regulatory Elements Full length NSPLP-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known NSPLP-encoding sequence "outward" generating amplicons containing new, unknown nucleotide sequence for the region of interest. The initial primers are designed from the CDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 $\mu$l aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 $\mu$l of ligation bligation buffer, 1 $\mu$l T4-DNA ligase (15 units) and 1 $\mu$l T4 polynucleotide kinase are added, and the mixture is incubated at room temperature for 2–3 hours or overnight at 16° C. Competent *E. coli* cells (in 40 $\mu$l of appropriate media) are transformed with 3 $\mu$l of ligation mixture and cultured in 80 $\mu$l of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 $\mu$l of liquid LB/2×Carb medium placed in an individual well of an appropriate, commercially-available, sterile 96-well microtiter plate. The following day, 5 $\mu$l of each overnight culture is transferred into a non-sterile 96-well plate and after dilution 1:10 with water, 5 $\mu$l of each sample is transferred into a PCR array.

For PCR amplification, 18 $\mu$l of concentrated PCR reaction mix (3.3x) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs.

Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N. H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The NSPLP-encoding sequence, or any part thereof, is used to inhibit in vivo or in vitro expression of naturally occurring NSPLP. Although use of antisense oligonucleotides, comprising about 20 base-pairs, is specifically described, essentially the same procedure is used with larger cDNA fragments. An oligonucleotide based on the coding sequences of NSPLP, as shown in FIGS. 1A, 1B, 1C, 2A, 2B and 2C is used to inhibit expression of naturally occurring NSPLP. The complementary oligonucleotide is designed from the most unique 5' sequence as shown in FIGS. 1A, 1B, 1C, 2A, 2B and 2C and used either to inhibit transcription by preventing promoter binding to the upstream nontranslated sequence or translation of an NSPLP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, 1C, 2A, 2B and 2C.

VIII Expression of NSPLP

Expression of the NSPLP is accomplished by subcloning the cDNAs into appropriate vectors and transfecting the vectors into host cells. In this case, the cloning vector, pSport, previously used for the generation of the cDNA library is used to express NSPLP in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length NSPLP-encoding sequence. The signal sequence directs the secretion of NSPLP into the bacterial growth media which can be used directly in the following assay for activity.

IX NSPLP Activity

NSPLP's ER targeting activity can be assessed by a method of van de Velde et al (1994, supra). Microsomes are collected from cells expressing NSPLP by a 100,000 g spin in a method described by Verboomen H et al (1992 Biochem J 286: 591–596). After treatment with 0.5M KCl and centrifugation the pellet is resuspended and subject to gel electrophoresis. Western blot analysis using antibodies to NSPLP reveals the presence of NSPLP in the ER membrane.

X Production of NSPLP Specific Antibodies

NSPLP substantially purified using PAGE electrophoresis (Sambrook, supra) is used to immunize rabbits and to produce antibodies using standard protocols. The amino acid sequence translated from NSPLP is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 7 and 8) is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring NSPLP Using Specific Antibodies

Naturally occurring or recombinant NSPLP is substantially purified by immunoaffinity chromatography using antibodies specific for NSPLP. An immunoaffinity column is constructed by covalently coupling NSPLP antibody to an activated chromatographic resin such as CnBr-activated Sepharose (Pharmacia Biotech). After the coupling, the resin is blocked and washed according to the manufacturer's instructions.

Media containing NSPLP is passed over the immunoaffinity column, and the column is washed under conditions that allow the preferential absorbance of NSPLP (eg, high ionic strength buffers in the presence of detergent). The column is eluted under conditions that disrupt antibody/NSPLP binding (eg, a buffer of pH 2–3 or a high concentration of a chaotrope such as urea or thiocyanate ion), and NSPLP is collected.

XII Identification of Molecules Which Interact with NSPLP

NSPLP, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled NSPLP, washed and any wells with labelled NSPLP complex are assayed. Data obtained using different concentrations of NSPLP are used to calculate values for the number, affinity, and association of NSPLP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. An isolated and purified polynucleotide sequence which encodes a protein having the amino acid sequence shown in SEQ ID NO:1.

2. An expression vector containing the polynucleotide sequence of claim 1.

3. A host cell comprising the expression vector of claim 2.

4. A method for producing a polypeptide comprising the amino acid sequence shown in SEQ ID NO:1, the method comprising the steps of:
   a) culturing the host cell of claim 3 under conditions suitable for the expression of the polypeptide; and
   b) recovering the polypeptide from the host cell culture.

5. An isolated and purified polynucleotide sequence consisting of the sequence of SEQ ID NO:2.

6. A polynucleotide sequence which is fully complementary to the sequence of SEQ ID NO:2.

7. An isolated and purified polynucleotide sequence which encodes a protein having the amino acid sequence shown in SEQ ID NO:3.

8. An expression vector containing the polynucleotide sequence of claim 7.

9. A host cell comprising the expression vector of claim 8.

10. A method for producing a polypeptide comprising the amino acid sequence shown in SEQ ID NO:3, the method comprising the steps of:
    a) culturing the host cell of claim 9 under conditions suitable for the expression of the polypeptide; and
    b) recovering the polypeptide from the host cell culture.

11. An isolated and purified polynucleotide sequence consisting of the sequence of SEQ ID NO:4.

12. A polynucleotide sequence which is fully complementary to the sequence of SEQ ID NO:4.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 199 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY:
        ( B ) CLONE: Consensus ( x i ) SEQUENCE DESCRIPTION: SEQ ID NO:1:

```
Met  Asp  Gly  Gln  Lys  Lys  Asn  Trp  Lys  Asp  Lys  Val  Val  Asp  Leu  Leu
 1              5                        10                       15
Tyr  Trp  Arg  Asp  Ile  Lys  Lys  Thr  Gly  Val  Val  Phe  Gly  Ala  Ser  Leu
              20                        25                       30
Phe  Leu  Leu  Leu  Ser  Leu  Thr  Val  Phe  Ser  Ile  Val  Ser  Val  Thr  Ala
         35                        40                       45
Tyr  Ile  Ala  Leu  Ala  Leu  Leu  Ser  Val  Thr  Ile  Ser  Phe  Arg  Ile  Tyr
    50                        55                       60
Lys  Gly  Val  Ile  Gln  Ala  Ile  Gln  Lys  Ser  Asp  Glu  Gly  His  Pro  Phe
 65                       70                       75                        80
Arg  Ala  Tyr  Leu  Glu  Ser  Glu  Val  Ala  Ile  Ser  Glu  Glu  Leu  Val  Gln
              85                        90                       95
Lys  Tyr  Ser  Asn  Ser  Ala  Leu  Gly  His  Val  Asn  Cys  Thr  Ile  Lys  Glu
             100                       105                      110
Leu  Arg  Arg  Leu  Phe  Leu  Val  Asp  Asp  Leu  Val  Asp  Ser  Leu  Lys  Phe
         115                       120                      125
Ala  Val  Leu  Met  Trp  Val  Phe  Thr  Tyr  Val  Gly  Ala  Leu  Phe  Asn  Gly
    130                       135                      140
Leu  Thr  Leu  Leu  Ile  Leu  Ala  Leu  Ile  Ser  Leu  Phe  Ser  Val  Pro  Val
145                       150                      155                       160
Ile  Tyr  Glu  Arg  His  Gln  Ala  Gln  Ile  Asp  His  Tyr  Leu  Gly  Leu  Ala
             165                       170                      175
Asn  Lys  Asn  Val  Lys  Asp  Ala  Met  Ala  Lys  Ile  Gln  Ala  Lys  Ile  Pro
             180                       185                      190
Gly  Leu  Lys  Arg  Lys  Ala  Glu
             195
```

( 2 ) INFORMATION FOR SEQ ID NO:2:

( i ) SEQUENCE CHARACTERISTICS:
        ( A ) LENGTH: 799 base pairs
        ( B ) TYPE: nucleic acid ( C ) STRANDEDNESS: single
( D ) TOPOLOGY: linear ( i i ) MOLECULE TYPE: cDNA ( v i i ) IMMEDIATE SOURCE:
( A ) LIBRARY:
( B ) CLONE: Consensus ( x i ) SEQUENCE DESCRIPTION: SEQ ID NO:2:

| | | | | | | |
|---|---|---|---|---|---|---|
| GGTTTGTGCA | GTTACAGCTT | TTCTNTTGGT | ATGCATAATT | AATANTTGGA | GCTGCAAAGA | 60 |
| GATCGTGACA | AGAGATGGAC | GGTCAGAAGA | AAAATTGGAA | GGACAAGGTT | GTTGACCTCC | 120 |
| TGTACTGGAG | AGACATTAAG | AAGACTGGAG | TGGTGTTTGG | TGCCAGCCTA | TTCCTGCTGC | 180 |
| TTTCATTGAC | AGTATTCAGC | ATTGTGAGCG | TAACAGCCTA | CATTGCCTTG | GCCCTGCTCT | 240 |
| CTGTGACCAT | CAGCTTTAGG | ATATACAAGG | GTGTGATCCA | AGCTATCCAG | AAATCAGATG | 300 |
| AAGGCCACCC | ATTCAGGGCA | TATCTGGAAT | CTGAAGTTGC | TATATCTGAG | GAGTTGGTTC | 360 |
| AGAAGTACAG | TAATTCTGCT | CTTGGTCATG | TGAACTGCAC | GATAAAGGAA | CTCAGGCGCC | 420 |
| TCTTCTTAGT | TGATGATTTA | GTTGATTCTC | TGAAGTTTGC | AGTGTTGATG | TGGGTATTTA | 480 |
| CCTATGTTGG | TGCCTTGTTT | AATGGTCTGA | CACTACTGAT | TTTGGCTCTC | ATTTCACTCT | 540 |
| TCAGTGTTCC | TGTTATTTAT | GAACGGCATC | AGGCACAGAT | AGATCATTAT | CTAGGACTTG | 600 |
| CAAATAAGAA | TGTTAAAGAT | GCTATGGCTA | AAATCCAAGC | AAAAATCCCT | GGATTGAAGC | 660 |
| GCAAAGCTGA | ATGAAAACGC | CCAAAATAAT | TAGTAGGAGT | TCATCTTTAA | AGGGGATATT | 720 |
| CATTTGATTA | TACGGGGGAG | GGTCAGGGAA | GAACGACCTT | GACGTTGCAG | TGCAGTTTCA | 780 |
| CAGATCGTTG | TTAGATCTT | | | | | 799 |

( 2 ) INFORMATION FOR SEQ ID NO:3:

( i ) SEQUENCE CHARACTERISTICS:
( A ) LENGTH: 241 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( A ) LIBRARY: THP1NOB01
( B ) CLONE: 31870

( x i ) SEQUENCE DESCRIPTION: SEQ ID NO:3:

| Met | Ala | Glu | Arg | Xaa | Ala | Ala | Thr | Gln | Ser | His | Ser | Ile | Ser | Ser | Ser |
|---|---|---|---|---|---|---|---|---|---|---|---|---|---|---|---|
| 1 | | | | 5 | | | | | 10 | | | | | 15 | |

| Ser | Phe | Gly | Ala | Glu | Pro | Ser | Ala | Pro | Gly | Gly | Gly | Gly | Ser | Pro | Gly |
|---|---|---|---|---|---|---|---|---|---|---|---|---|---|---|---|
| | | | 20 | | | | | 25 | | | | | 30 | | |

| Ala | Cys | Pro | Ala | Leu | Gly | Thr | Lys | Ser | Cys | Ser | Ser | Ser | Cys | Ala | Val |
|---|---|---|---|---|---|---|---|---|---|---|---|---|---|---|---|
| | | 35 | | | | | 40 | | | | | 45 | | | |

| His | Asp | Leu | Ile | Xaa | Trp | Arg | Asp | Val | Lys | Lys | Thr | Gly | Phe | Val | Phe |
|---|---|---|---|---|---|---|---|---|---|---|---|---|---|---|---|
| | 50 | | | | | 55 | | | | | 60 | | | | |

| Gly | Thr | Thr | Leu | Ile | Met | Leu | Leu | Ser | Leu | Ala | Ala | Phe | Ser | Val | Ile |
|---|---|---|---|---|---|---|---|---|---|---|---|---|---|---|---|
| 65 | | | | | 70 | | | | | 75 | | | | | 80 |

| Ser | Val | Val | Ser | Tyr | Leu | Ile | Leu | Ala | Leu | Leu | Ser | Val | Thr | Ile | Ser |
|---|---|---|---|---|---|---|---|---|---|---|---|---|---|---|---|
| | | | | 85 | | | | | 90 | | | | | 95 | |

| Phe | Arg | Ile | Tyr | Lys | Ser | Val | Ile | Gln | Ala | Val | Gln | Lys | Ser | Glu | Glu |
|---|---|---|---|---|---|---|---|---|---|---|---|---|---|---|---|
| | | | | 100 | | | | | 105 | | | | | 110 | |

| Gly | His | Pro | Phe | Lys | Ala | Tyr | Leu | Asp | Val | Asp | Ile | Thr | Leu | Ser | Ser |
|---|---|---|---|---|---|---|---|---|---|---|---|---|---|---|---|
| | | | 115 | | | | | 120 | | | | | 125 | | |

| | | | | | | | | | | | | | |
|---|---|---|---|---|---|---|---|---|---|---|---|---|---|
|Glu|Ala|Phe|His|Asn|Tyr|Met|Asn|Ala|Ala|Met|Val|His|Ile Asn Arg|
| |130| | | |135| | | |140| | | | |
|Ala|Leu|Lys|Leu|Ile|Ile|Arg|Leu|Phe|Leu|Val|Glu|Asp|Leu Val Asp|
|145| | | |150| | | |155| | | | |160|
|Ser|Leu|Lys|Leu|Ala|Val|Phe|Met|Trp|Leu|Met|Thr|Tyr|Val Gly Ala|
| | | | |165| | | |170| | | | |175|
|Val|Phe|Asn|Gly|Ile|Thr|Leu|Leu|Ile|Leu|Ala|Glu|Leu|Leu Ile Xaa|
| | | |180| | | | |185| | | |190| |
|Ser|Val|Pro|Ile|Val|Tyr|Xaa|Lys|Tyr|Lys|Val|Pro|Ser|Lys Thr Pro|
| | |195| | | | |200| | | |205| | |
|Trp|Asn|Arg|Gln|Lys|Lys|Gly|Arg|Ile|Ser|Thr|Trp|Lys|Pro Glu Met|
| |210| | | | |215| | | |220| | | |
|Gln|Gln|Leu|Leu|Lys|His|His|Leu|Ile|Val|Ile|Thr|Ser|Leu Leu Val|
|225| | | | |230| | | |235| | | |240|
|Leu| | | | | | | | | | | | | |

( 2 ) INFORMATION FOR SEQ ID NO:4:

( i ) SEQUENCE CHARACTERISTICS:
( A ) LENGTH: 1095 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: THP1NOB01
( B ) CLONE: 31870

( x i ) SEQUENCE DESCRIPTION: SEQ ID NO:4:

| | | | | | |
|---|---|---|---|---|---|
|ACACNAGCGN|NTCGNGCTCC|CGAACCTCTA|GCTGCGACTC|GGANTGAGTC|AGTCAGTCTG 60|
|TCGGAGTCTG|TCCTCGGAGC|AGGCGGAGTA|AAGGGACTTG|AGCGAGCCAG|TTGCCGGATT 120|
|ATTCTATTTC|CCCTCCCTCT|CTCCCGCCCC|GTATCTCTTT|TCATTTTNNT|NCCACCCTTG 180|
|CTCGCGTANC|ATGGCGGAGC|GTNCGGCGGC|CACTCAGTCC|CATTCCATCT|CCTCGTCGTC 240|
|CTTCGGAGCC|GAGCCGTCCG|CGCCCGGCGG|CGGCGGGAGC|CCAGGAGCCT|GCCCCGCCCT 300|
|GGGGACGAAG|AGCTGCAGCT|CCTCCTGTGC|GGTGCACGAT|CTGATTTTMT|GGAGAGATGT 360|
|GAAGAAGACT|GGGTTTGTCT|TTGGCACCAC|GCTGATCATG|CTGCTTTCCC|TGGCAGCTTT 420|
|CAGTGTCATC|AGTGTGGTTT|CTTACCTCAT|CCTGGCTCTT|CTCTCTGTCA|CCATCAGCTT 480|
|CAGGATCTAC|AAGTCCGTCA|TCCAAGCTGT|ACAGAAGTCA|GAAGAAGGCC|ATCCATTCAA 540|
|AGCCTACCTG|GACGTAGACA|TTACTCTGTC|CTCAGAAGCT|TTCCATAATT|ACATGAATGC 600|
|TGCCATGGTG|CACATCAACA|GGGCCCTGAA|ACTCATTATT|CGTCTCTTTC|TGGTAGAAGA 660|
|TCTGGTTGAC|TCCTTGAAGC|TGGCTGTCTT|CATGTGGCTG|ATGACCTATG|TTGGTGCTGT 720|
|TTTTAACGGA|ATCACCCTTC|TAATTCTTGC|TGAACTGCTC|ATTTTNAGTG|TCCCGATTGT 780|
|NTATNAGAAG|TACAAGGTTC|CAAGCAAAAC|TCCCTGGAAT|CGCCAAAAAA|AAGGCAGAAT 840|
|AAGTACATGG|AAACCAGAAA|TGCAACAGTT|ACTAAAACAC|CATTTAATAG|TTATAACGTC 900|
|GTTACTTGTA|CTATGAAGGA|AAATACTCAG|TGTCAGCTTG|AGCCTGCATT|CCAAGCTTTT 960|
|TTTTTAATTT|GGTGGTTTTC|TCCCATCCTT|TCCCTTTAAC|CCTCAGTNTC|AAGCACAAAN 1020|
|TTTNATGGAC|TGATAANNGA|TCTATNTTAG|ANCTCAGAAG|ANGANAGNTT|CANNTGCATA 1080|
|GGNTAAGGNA|NTACC| | | |1095|

( 2 ) INFORMATION FOR SEQ ID NO:5:

( i ) SEQUENCE CHARACTERISTICS:
    ( A ) LENGTH: 776 amino acids
    ( B ) TYPE: amino acid
    ( C ) STRANDEDNESS: single
    ( D ) TOPOLOGY: linear ( i i ) MOLECULE TYPE: peptide ( v i i ) IMMEDIATE SOURCE:
    ( A ) LIBRARY: GenBank
    ( B ) CLONE: 307307

( x i ) SEQUENCE DESCRIPTION: SEQ ID NO:5:

```
Met Ala Ala Pro Gly Asp Pro Gln Asp Glu Leu Leu Pro Leu Ala Gly
 1               5                  10                  15
Pro Gly Ser Gln Trp Leu Arg His Arg Gly Glu Gly Glu Asn Glu Ala
            20                  25                  30
Val Thr Pro Lys Gly Ala Thr Pro Ala Pro Gln Ala Gly Glu Pro Ser
        35                  40                  45
Pro Gly Leu Gly Ala Arg Ala Arg Glu Ala Ala Ser Arg Glu Ala Gly
    50                  55                  60
Ser Gly Pro Ala Arg Gln Ser Pro Val Ala Met Glu Thr Ala Ser Thr
65                  70                  75                  80
Gly Val Ala Gly Val Ser Ser Ala Met Asp His Thr Phe Ser Thr Thr
                85                  90                  95
Ser Lys Asp Gly Glu Gly Ser Cys Tyr Thr Ser Leu Ile Ser Asp Ile
                100                 105                 110
Cys Tyr Pro Pro Gln Glu Asp Ser Thr Tyr Phe Thr Gly Ile Leu Gln
            115                 120                 125
Lys Glu Asn Gly His Val Thr Ile Ser Glu Ser Pro Glu Glu Leu Gly
    130                 135                 140
Thr Pro Gly Pro Ser Leu Pro Asp Val Pro Gly Ile Glu Ser Arg Gly
145                 150                 155                 160
Leu Phe Ser Ser Asp Ser Gly Ile Glu Met Thr Pro Ala Glu Ser Thr
                165                 170                 175
Glu Val Asn Lys Ile Leu Ala Asp Pro Leu Asp Gln Met Lys Ala Glu
                180                 185                 190
Ala Tyr Lys Tyr Ile Asp Ile Thr Arg Pro Glu Glu Val Lys His Gln
            195                 200                 205
Glu Gln His His Pro Glu Leu Glu Asp Lys Asp Leu Asp Phe Lys Asn
    210                 215                 220
Lys Asp Thr Asp Ile Ser Ile Lys Pro Glu Gly Val Arg Glu Pro Asp
225                 230                 235                 240
Lys Pro Ala Pro Val Glu Gly Lys Ile Ile Lys Asp His Leu Leu Glu
                245                 250                 255
Glu Ser Thr Phe Ala Pro Tyr Ile Asp Asp Leu Ser Glu Glu Gln Arg
                260                 265                 270
Arg Ala Pro Gln Ile Thr Thr Pro Val Lys Ile Thr Leu Thr Glu Ile
            275                 280                 285
Glu Pro Ser Val Glu Thr Thr Thr Gln Glu Lys Thr Pro Glu Lys Gln
    290                 295                 300
Asp Ile Cys Leu Lys Pro Ser Pro Asp Thr Val Pro Thr Val Thr Val
305                 310                 315                 320
Ser Glu Pro Glu Asp Asp Ser Pro Gly Ser Ile Thr Pro Pro Ser Ser
                325                 330                 335
Gly Thr Glu Pro Ser Ala Ala Glu Ser Gln Gly Lys Gly Ser Ile Ser
                340                 345                 350
```

```
Glu  Asp  Glu  Leu  Ile  Thr  Ala  Ile  Lys  Glu  Ala  Lys  Gly  Leu  Ser  Tyr
          355                      360                     365

Glu  Thr  Ala  Glu  Asn  Pro  Arg  Pro  Val  Gly  Gln  Leu  Ala  Asp  Arg  Pro
     370                     375                     380

Glu  Val  Lys  Ala  Arg  Ser  Gly  Pro  Pro  Thr  Ile  Pro  Ser  Pro  Leu  Asp
385                      390                     395                     400

His  Glu  Ala  Ser  Ser  Ala  Glu  Ser  Gly  Asp  Ser  Glu  Ile  Glu  Leu  Val
               405                     410                     415

Ser  Glu  Asp  Pro  Met  Ala  Ala  Glu  Asp  Ala  Leu  Pro  Ser  Gly  Tyr  Val
               420                     425                     430

Ser  Phe  Gly  His  Val  Gly  Gly  Pro  Pro  Ser  Pro  Ala  Ser  Pro  Ser
               435                     440                     445

Ile  Gln  Tyr  Ser  Ile  Leu  Arg  Glu  Glu  Arg  Glu  Ala  Glu  Leu  Asp  Ser
          450                     455                     460

Glu  Leu  Ile  Ile  Glu  Ser  Cys  Asp  Ala  Ser  Ser  Ala  Ser  Glu  Glu  Ser
465                           470                     475                     480

Pro  Lys  Arg  Glu  Gln  Asp  Ser  Pro  Pro  Met  Lys  Pro  Ser  Ala  Leu  Asp
                    485                     490                     495

Ala  Ile  Arg  Glu  Glu  Thr  Gly  Val  Arg  Ala  Glu  Glu  Arg  Ala  Pro  Ser
               500                     505                     510

Arg  Arg  Gly  Leu  Ala  Glu  Pro  Gly  Ser  Phe  Leu  Asp  Tyr  Pro  Ser  Thr
          515                     520                     525

Glu  Pro  Gln  Pro  Gly  Pro  Glu  Leu  Pro  Pro  Gly  Asp  Gly  Ala  Leu  Glu
     530                     535                     540

Pro  Glu  Thr  Pro  Met  Leu  Pro  Arg  Lys  Pro  Glu  Glu  Asp  Ser  Ser  Ser
545                      550                     555                     560

Asn  Gln  Ser  Pro  Ala  Ala  Thr  Lys  Gly  Pro  Gly  Pro  Leu  Gly  Pro  Gly
               565                     570                     575

Ala  Pro  Pro  Pro  Leu  Leu  Phe  Leu  Asn  Lys  Gln  Lys  Ala  Ile  Asp  Leu
               580                     585                     590

Leu  Tyr  Trp  Arg  Asp  Ile  Lys  Gln  Thr  Gly  Ile  Val  Phe  Gly  Ser  Phe
          595                     600                     605

Leu  Leu  Leu  Leu  Phe  Ser  Leu  Thr  Gln  Phe  Ser  Val  Val  Ser  Val  Val
          610                     615                     620

Ala  Tyr  Leu  Ala  Leu  Ala  Leu  Ser  Ala  Thr  Ile  Ser  Phe  Arg  Ile
625                      630                     635                     640

Tyr  Lys  Ser  Val  Leu  Gln  Ala  Val  Gln  Lys  Thr  Asp  Glu  Gly  His  Pro
               645                     650                     655

Phe  Lys  Ala  Tyr  Leu  Glu  Leu  Glu  Ile  Thr  Leu  Ser  Gln  Glu  Gln  Ile
               660                     665                     670

Gln  Lys  Tyr  Thr  Asp  Cys  Leu  Gln  Phe  Tyr  Val  Asn  Ser  Thr  Leu  Lys
          675                     680                     685

Glu  Leu  Arg  Arg  Leu  Phe  Leu  Val  Gln  Asp  Leu  Val  Asp  Ser  Leu  Lys
     690                     695                     700

Phe  Ala  Val  Leu  Met  Trp  Leu  Leu  Thr  Tyr  Val  Gly  Ala  Leu  Phe  Asn
705                      710                     715                     720

Gly  Leu  Thr  Leu  Leu  Leu  Met  Ala  Val  Val  Ser  Met  Phe  Thr  Leu  Pro
               725                     730                     735

Val  Val  Tyr  Val  Lys  His  Gln  Ala  Gln  Ile  Asp  Gln  Tyr  Leu  Gly  Leu
               740                     745                     750

Val  Arg  Thr  His  Ile  Asn  Ala  Val  Val  Ala  Lys  Ile  Gln  Ala  Lys  Ile
          755                     760                     765

Pro  Gly  Ala  Lys  Arg  His  Ala  Glu
```

(2) INFORMATION FOR SEQ ID NO:6:

(i) SEQUENCE CHARACTERISTICS:
        (A) LENGTH: 356 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 307309

(xi) SEQUENCE DESCRIPTION: SEQ ID NO:6:

```
Met  Ala  Ala  Glu  Asp  Ala  Leu  Pro  Ser  Gly  Tyr  Val  Ser  Phe  Gly  His
 1                    5                        10                       15

Val  Gly  Gly  Pro  Pro  Ser  Pro  Ala  Ser  Pro  Ser  Ile  Gln  Tyr  Ser
                20                       25                       30

Ile  Leu  Arg  Glu  Glu  Arg  Glu  Ala  Glu  Leu  Asp  Ser  Glu  Leu  Ile  Ile
               35                        40                       45

Glu  Ser  Cys  Asp  Ala  Ser  Ser  Ala  Ser  Glu  Glu  Ser  Pro  Lys  Arg  Glu
      50                        55                       60

Gln  Asp  Ser  Pro  Pro  Met  Lys  Pro  Ser  Ala  Leu  Asp  Ala  Ile  Arg  Glu
 65                       70                       75                       80

Glu  Thr  Gly  Val  Arg  Ala  Glu  Glu  Arg  Ala  Pro  Ser  Arg  Arg  Gly  Leu
                    85                       90                       95

Ala  Glu  Pro  Gly  Ser  Phe  Leu  Asp  Tyr  Pro  Ser  Thr  Glu  Pro  Gln  Pro
                    100                      105                      110

Gly  Pro  Glu  Leu  Pro  Pro  Gly  Asp  Gly  Ala  Leu  Glu  Pro  Glu  Thr  Pro
                115                      120                      125

Met  Leu  Pro  Arg  Lys  Pro  Glu  Glu  Asp  Ser  Ser  Ser  Asn  Gln  Ser  Pro
     130                      135                      140

Ala  Ala  Thr  Lys  Gly  Pro  Gly  Pro  Leu  Gly  Pro  Gly  Ala  Pro  Pro  Pro
145                           150                      155                 160

Leu  Leu  Phe  Leu  Asn  Lys  Gln  Lys  Ala  Ile  Asp  Leu  Leu  Tyr  Trp  Arg
               165                      170                      175

Asp  Ile  Lys  Gln  Thr  Gly  Ile  Val  Phe  Gly  Ser  Phe  Leu  Leu  Leu  Leu
               180                      185                      190

Phe  Ser  Leu  Thr  Gln  Phe  Ser  Val  Val  Ser  Val  Val  Ala  Tyr  Leu  Ala
               195                      200                      205

Leu  Ala  Ala  Leu  Ser  Ala  Thr  Ile  Ser  Phe  Arg  Ile  Tyr  Lys  Ser  Val
     210                      215                      220

Leu  Gln  Ala  Val  Gln  Lys  Thr  Asp  Glu  Gly  His  Pro  Phe  Lys  Ala  Tyr
225                      230                      235                      240

Leu  Glu  Leu  Glu  Ile  Thr  Leu  Ser  Gln  Glu  Gln  Ile  Gln  Lys  Tyr  Thr
               245                      250                      255

Asp  Cys  Leu  Gln  Phe  Tyr  Val  Asn  Ser  Thr  Leu  Lys  Glu  Leu  Arg  Arg
               260                      265                      270

Leu  Phe  Leu  Val  Gln  Asp  Leu  Val  Asp  Ser  Leu  Lys  Phe  Ala  Val  Leu
     275                      280                      285

Met  Trp  Leu  Leu  Thr  Tyr  Val  Gly  Ala  Leu  Phe  Asn  Gly  Leu  Thr  Leu
     290                      295                      300

Leu  Leu  Met  Ala  Val  Val  Ser  Met  Phe  Thr  Leu  Pro  Val  Val  Tyr  Val
305                      310                      315                      320

Lys  His  Gln  Ala  Gln  Ile  Asp  Gln  Tyr  Leu  Gly  Leu  Val  Arg  Thr  His
```

325                          330                             335

Ile  Asn  Ala  Val  Val  Ala  Lys  Ile  Gln  Ala  Lys  Ile  Pro  Gly  Ala  Lys
                        340                          345                        350

Arg  His  Ala  Glu
                   355

( 2 ) INFORMATION FOR SEQ ID NO:7:

( i ) SEQUENCE CHARACTERISTICS:
        ( A ) LENGTH: 208 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 307311

( x i ) SEQUENCE DESCRIPTION: SEQ ID NO:7:

Met  Gln  Ala  Thr  Ala  Asp  Ser  Thr  Lys  Met  Asp  Cys  Val  Trp  Ser  Asn
    1                       5                          10                          15

Trp  Lys  Ser  Gln  Ala  Ile  Asp  Leu  Leu  Tyr  Trp  Arg  Asp  Ile  Lys  Gln
                        20                          25                          30

Thr  Gly  Ile  Val  Phe  Gly  Ser  Phe  Leu  Leu  Leu  Leu  Phe  Ser  Leu  Thr
                   35                          40                          45

Gln  Phe  Ser  Val  Val  Ser  Val  Val  Ala  Tyr  Leu  Ala  Leu  Ala  Ala  Leu
              50                          55                          60

Ser  Ala  Thr  Ile  Ser  Phe  Arg  Ile  Tyr  Lys  Ser  Val  Leu  Gln  Ala  Val
    65                          70                          75                          80

Gln  Lys  Thr  Asp  Glu  Gly  His  Pro  Phe  Lys  Ala  Tyr  Leu  Glu  Leu  Glu
                             85                          90                          95

Ile  Thr  Leu  Ser  Gln  Glu  Gln  Ile  Gln  Lys  Tyr  Thr  Asp  Cys  Leu  Gln
                        100                         105                         110

Phe  Tyr  Val  Asn  Ser  Thr  Leu  Lys  Glu  Leu  Arg  Arg  Leu  Phe  Leu  Val
                   115                         120                         125

Gln  Asp  Leu  Val  Asp  Ser  Leu  Lys  Phe  Ala  Val  Leu  Met  Trp  Leu  Leu
              130                         135                         140

Thr  Tyr  Val  Gly  Ala  Leu  Phe  Asn  Gly  Leu  Thr  Leu  Leu  Leu  Met  Ala
    145                         150                         155                         160

Val  Val  Ser  Met  Phe  Thr  Leu  Pro  Val  Val  Tyr  Val  Lys  His  Gln  Ala
                             165                         170                         175

Gln  Ile  Asp  Gln  Tyr  Leu  Gly  Leu  Val  Arg  Thr  His  Ile  Asn  Ala  Val
                        180                         185                         190

Val  Ala  Lys  Ile  Gln  Ala  Lys  Ile  Pro  Gly  Ala  Lys  Arg  His  Ala  Glu
                   195                         200                         205

( 2 ) INFORMATION FOR SEQ ID NO:8:

( i ) SEQUENCE CHARACTERISTICS:
        ( A ) LENGTH: 267 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 281046

( x i ) SEQUENCE DESCRIPTION: SEQ ID NO:8:

```
Met  Asp  Cys  Val  Trp  Ser  Asn  Trp  Lys  Ser  Gln  Ala  Ile  Asp  Leu  Leu
 1              5                   10                       15
Tyr  Trp  Arg  Asp  Ile  Lys  Gln  Thr  Gly  Ile  Val  Phe  Gly  Ser  Phe  Leu
                20                  25                       30
Leu  Leu  Leu  Phe  Ser  Leu  Thr  Gln  Phe  Ser  Val  Val  Ser  Val  Val  Ala
           35                       40                  45
Tyr  Leu  Ala  Leu  Ala  Ala  Leu  Ser  Ala  Thr  Ile  Ser  Phe  Arg  Ile  Tyr
      50                       55                   60
Lys  Ser  Val  Leu  Gln  Ala  Val  Gln  Lys  Thr  Asp  Glu  Gly  His  Pro  Phe
 65                       70                  75                            80
Lys  Ala  Tyr  Leu  Glu  Leu  Glu  Ile  Thr  Leu  Ser  Gln  Glu  Gln  Ile  Gln
                     85                       90                       95
Lys  Tyr  Thr  Asp  Cys  Leu  Gln  Leu  Tyr  Val  Asn  Ser  Thr  Leu  Lys  Glu
               100                       105                      110
Leu  Arg  Arg  Leu  Phe  Leu  Val  Gln  Asp  Leu  Val  Asp  Ser  Leu  Lys  Phe
          115                       120                      125
Ala  Val  Leu  Met  Trp  Leu  Leu  Thr  Tyr  Val  Gly  Ala  Leu  Phe  Asn  Gly
     130                       135                 140
Leu  Thr  Leu  Leu  Leu  Met  Ala  Val  Val  Ser  Met  Phe  Thr  Leu  Pro  Val
145                      150                      155                      160
Val  Tyr  Val  Lys  His  Gln  Ala  Gln  Val  Asp  Gln  Tyr  Leu  Gly  Leu  Val
               165                       170                      175
Arg  Thr  His  Ile  Asn  Thr  Val  Val  Ala  Lys  Ile  Gln  Ala  Lys  Ile  Pro
               180                       185                      190
Gly  Ala  Arg  Gly  Met  Leu  Ser  Arg  Trp  Leu  Pro  Gln  Glu  Lys  Pro  Asp
          195                       200                      205
Met  Asn  Gly  Gly  Val  Trp  Ser  Gly  Asn  Ser  Ser  Leu  Leu  Pro  Arg  Tyr
     210                       215                      220
Cys  Glu  Leu  Ile  Val  Ser  Leu  Pro  Gln  Tyr  His  Asn  Leu  Arg  Gly  Lys
225                      230                      235                      240
Leu  Arg  Asp  Arg  Cys  Phe  Gln  Ser  Phe  Pro  Val  Leu  Leu  Gly  Tyr  Leu
                245                       250                      255
Ser  Pro  Pro  Arg  Pro  Leu  Ser  Ser  Thr  Lys  Val
               260                       265
```

( 2 ) INFORMATION FOR SEQ ID NO:9:

( i ) SEQUENCE CHARACTERISTICS:
        ( A ) LENGTH: 261 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: SPLNFET01
        ( B ) CLONE: 28742

( x i ) SEQUENCE DESCRIPTION: SEQ ID NO:9:

```
CCTATNCCNG  CTGCTTTCAT  TGACAGTATT  CAGCATTGTG  AGCGTAACAG  CCTACATTGC      60
CTTNGCCCTG  CNCTCTGTGA  CCATCAGCTN  TAGGCTATAC  AAGGGTGTGA  TCCAAGCTAT     120
CCAGAAATCA  GATGAAGGNC  ACCCATTCAG  GGCATATCTG  GANTCTGAAG  TTGCTATATC     180
TGAGGAGTTG  NTTCAGAAGT  ACACGTAAAT  NNTGNNCNTG  GTCAATGTGA  NCTCCACGNC     240
TAANGGANCT  CAGGTGCCTA  T                                                  261
```